(12) United States Patent
Toledo et al.

(10) Patent No.: US 7,977,056 B2
(45) Date of Patent: Jul. 12, 2011

(54) METHODS OF IDENTIFYING STIMULANTS FOR BIOGENIC METHANE PRODUCTION FROM HYDROCARBON-BEARING FORMATIONS

(75) Inventors: Gerardo Vicente Toledo, San Diego, CA (US); Toby Howard Richardson, San Diego, CA (US); Ulrich Stingl, San Diego, CA (US); Eric J. Mathur, Encinitas, CA (US); J. Craig Venter, La Jolla, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 38 days.

(21) Appl. No.: 12/464,832

(22) Filed: May 12, 2009

(65) Prior Publication Data
US 2010/0047793 A1    Feb. 25, 2010

Related U.S. Application Data

(60) Provisional application No. 61/052,624, filed on May 12, 2008.

(51) Int. Cl.
*C12Q 1/68* (2006.01)
*C12P 5/02* (2006.01)
*C12N 1/00* (2006.01)
*E21B 43/22* (2006.01)
*E21B 43/16* (2006.01)

(52) U.S. Cl. ............ 435/6; 166/246; 166/401; 435/167; 435/243

(58) Field of Classification Search .................. None
See application file for complete search history.

(56) References Cited

U.S. PATENT DOCUMENTS

| | | | |
|---|---|---|---|
| 6,156,946 A * | 12/2000 | Coyle et al. | 585/264 |
| 2007/0248531 A1 * | 10/2007 | Debryun et al. | 423/650 |
| 2007/0251146 A1 * | 11/2007 | Larter et al. | 48/127.5 |

* cited by examiner

*Primary Examiner* — Christian Fronda
(74) *Attorney, Agent, or Firm* — DLA Piper LLP (US)

(57) ABSTRACT

The present invention describes methods of identifying stimulants for the biogenic production of methane in hydrocarbon-bearing formations. Methods involve the use of microbial nucleic acid sequence information for the determination of gene products that are enzymes in a variety of pathways involved in the conversion of hydrocarbons to methane. Enzymes and stimulants identified by invention methods can be used in processes for enhancing biogenic methane production, for example, by addition to coal seams and coalbed methane wells.

11 Claims, 17 Drawing Sheets

METHODS OF IDENTIFYING STIMULANTS FOR BIOGENIC METHANE PRODUCTION FROM HYDROCARBON-BEARING FORMATIONS

CROSS-REFERENCE TO RELATED APPLICATION

This application claims priority to U.S. provisional application No. 61/052,624, filed May 12, 2008, which is herein incorporated by reference in its entirety.

BACKGROUND OF THE INVENTION

The present invention relates generally to the molecular characterization of indigenous methane-producing microorganisms and defined assemblages thereof from hydrocarbon-bearing formations, such coal seams; and more specifically, to the analyses of environmental genomic data from such microorganisms, and the use of such data and microorganisms to enhance conversion and recovery of methane using stimulants identified by determining the presence of enzymes in pathways involved in the conversion of a hydrocarbon to methane.

Coalbed methane (CBM) is a source of natural gas produced either biologically or thermogenically in coal deposits. Biogenic production of CBM is the result of microbial metabolism and the degradation of coal with a subsequent electron flow among multiple microbial populations. Thermogenic production of CBM is the result of thermal cracking of sedimentary organic matter or oil, occurring later in coalification when temperatures rise above levels at which the methane-producing microorganisms can live. In coalbeds, pressure from overlying rock and surrounding water cause the CBM to bond to the surface of the coal and be absorbed into the solid matrix of the coal as free gas within micropores and cleats (natural fractures in the coal), as dissolved gas in water, as adsorbed gas held by molecular attraction on surfaces of macerals (organic constituents that comprise the coal mass), micropores, and cleats in the coal, and as absorbed gas within the molecular structure of the coal.

Coal is a sedimentary rock with various degrees of permeability, with methane residing primarily in the cleats. These fractures in the coal act as the major channels to allow CBM to flow. To extract the CBM, a steel-encased hole is drilled into the coal seam, which allows the pressure to decline due to the hole to the surface or the pumping of small amounts of water from the coalbed (dewatering). CBM has very low solubility in water and readily separates as pressure decreases, allowing it to be piped out of the well separately from the water. The CBM is then sent to a compressor station and into natural gas pipelines.

CBM represents a significant portion of the natural gas produced in the United States, estimated as providing approximately 10% of the natural gas supplies, or about 1.8 trillion cubic feet (TCF). International reserves provide enormous opportunity for future CBM production. Among the most productive areas is the San Juan Basin, located in Colorado and New Mexico. Based on such enormous reservoirs of CBM, minimal improvements in CBM recovery could thus result in significantly increased production from a well, and accordingly, a variety of methods are being developed to improve the recovery of CBM from coal seams.

Purely physical interventions can include optimizing drilling and fracturing methods. Other improvement methods involve the application of external factors directly onto the coalbeds. These include, for example, the injection of gases such as nitrogen (see, e.g., Shimizu, S., Akiyama, M., Naganuma, T., Fujioka, M., Nako, M. and Ishijima, Y. 2007. Molecular characterization of microbial communities in deep coal seam groundwater of northern Japan. Geobiology 5(4): 423-433; U.S. Pat. No. 4,883,122) and $CO_2$ (see, e.g., U.S. Pat. No. 5,402,847); and the injection of hot fluids such as water or steam (see, e.g., U.S. Pat. No. 5,072,990). Various methods are intended to increase the permeability of the coalbed seams either physically (see, e.g., U.S. Pat. No. 5,014,788) or chemically (see, e.g., U.S. Pat. No. 5,865,248).

More recently, improvement methods are being developed to enhance biogenic methane production from existing wells. U.S. Pat. No. 5,424,195 discloses the use of a consortium of microorganisms cultured in situ or on a coal-containing substrate to biologically convert coal to methane. PCT/GB2006/004443 (WO2007/060473) discloses methods of producing and using a culture of subterranean microorganisms. PCT/US2006/039352 (WO2008/041990) discloses methods and systems for stimulating biogenic production by introducing an injection fluid which facilitates anaerobic biological degradation of the non-liquid hydrocarbon layer by indigenous microorganisms. PCT/US2007/080161 (WO2008/042888) discloses methods comprising in situ heating of a non-liquid hydrocarbon layer to allow biogenic production of methane. U.S. Pat. No. 7,426,960 discloses methods to stimulate biogenic production of a metabolite with enhanced hydrogen content comprising injecting water into an opening to disperse a consortium of microorganisms therein. U.S. Pat. No. 6,543,535 discloses processes for stimulating the activity of microbial consortia in a hydrocarbon-bearing, subterranean formation to convert hydrocarbons to methane by using information obtained from analyzing components of the formation and characterizing the microorganisms of the consortia. Although U.S. Pat. No. 6,543,535 contemplates comparing isolated microorganisms to known microorganisms to establish phylogenetic identity to such known organisms, it does not disclose the identification or use of specific genes encoding enzymes involved in the biotransformation of coal to methane from methanogenic bacteria within the consortia, or the use of enzyme analysis to identify novel stimulants. U.S. Patent Application Publication No. 2008/0289816 discloses processes for introducing microorganisms to carbonaceous material in an anaerobic environment and for increasing biogenic hydrocarbon production comprising the use of amended formation water. U.S. Patent Application Publication No. 2008/0299635 discloses methods for stimulating methane production from a carbonaceous material with a methanogenic consortium. U.S. Patent Application Publication No. 2009/0023612 discloses methods of increasing biogenic production of fuel gas from carbonaceous material comprising the use of an anaerobic consortium including a *Pseudomonas* species. U.S. Patent Application Publication No. 2009/0023611 discloses isolated microbial consortia for biogenically producing methane from complex hydrocarbons comprising a *Thermotoga* species. U.S. Patent Application Publication No. 2008/0286855 discloses a method of increasing production of materials with enhanced hydrogen content comprising introducing a consortium comprising an isolated culture of *Thermacetogenium phaeum*. U.S. Pat. No. 7,416,879 discloses methods of stimulating biological activity of *Thermacetogenium phaeum* in a geologic formation comprising adding an amendment to the formation. U.S. Patent Application Publication No. 2008/0182318 discloses isolated microbial consortia for biogenic methane production comprising a *Desulfuromonas* species. U.S. Patent Application Publication No. 2007/0295505 discloses methods of stimulating biogenic production of a metabolic product with enhanced hydrogen content in a geologic formation that includes a carbonaceous material comprising providing a phosphorous compound to microorganisms therein. U.S. Patent Application Publication No. 2007/0261843 discloses methods of stimulating biogenic production of a metabolic product with enhanced hydrogen content in a geologic formation that includes a carbonaceous material comprising providing hydrogen and phosphorous compound to microorganisms therein. PCT/US2006/031723 (WO2007/022122) discloses systems for enhanced biogenic methane production comprising amending CBM water and other microbe-containing media, diminishing sulfate reduction competition, and enhancing organic matter concentrations.

Biogenic production of methane is the product of multiple possible enzymatic pathways that successively break down complex macromolecular, polycyclic, lignin-derived organic matter. For example, ligninolytic enzymes may include peroxidases (manganese peroxidase, lignin peroxidases, etc.), phenol oxidases (laccases), hydrolases, esterases, and oxidases (see, e.g., Fakoussa, R. M. and Hofrichter, M. 1999. Biotechnology and Microbiology of Coal Degradation. Appl. Microbiol. Biotechnol. 52:25-40). Once initial fragmentation occurs, enzymes involved in demethylation and ring cleavage, oxidation of aromatic and aliphatic moieties, and subsequent fermentation and methanogenesis pathways become involved. It is believed that microorganisms present in hydrocarbon-bearing formations, including methanogens, are obligate anaerobes.

There remains a need in the art to effectively stimulate biogenic production in hydrocarbon-bearing formations such as coal and to enhance the CBM productivity of existing wells. The present invention provides methods not only for the identification and use of microorganisms present in the formation environment, but for the identification of tailored interventions (such as stimulants that can be introduced into the environment to enhance the biogenic production of methane) after establishing the presence of specific gene products involved in metabolic pathways leading to methane production.

BRIEF SUMMARY OF THE INVENTION

The present invention provides methods and processes for the identification and use of stimulants and enzymes for biogenic production of methane in hydrocarbon-bearing formations. Invention methods comprise the use of nucleic acid information obtained from a variety of microorganisms identified in the hydrocarbon-bearing formation to identify gene products that are enzymes present in the microorganisms that can function in a variety of pathways starting from the hydrocarbon source and leading to methane production. See, for example, FIG. 1.

In a first aspect, the invention provides methods of identifying a stimulant that increases biogenic production of methane in a hydrocarbon-bearing formation that comprise: (a) obtaining a nucleic acid sequence from one or more microorganisms derived from a hydrocarbon-bearing formation environment; (b) determining the presence of one or more gene product of said nucleic acid sequence, wherein the gene product is an enzyme in a pathway involved in the conversion of a hydrocarbon to methane; and (c) identifying a substrate, reactant or co-factor of said enzyme that increases methane production when provided to one or more microorganisms in said hydrocarbon-bearing formation.

In one embodiment, one or more microorganisms from the hydrocarbon-bearing formation are enriched by selecting for the ability to grow on coal as the sole carbon source.

In another embodiment, step (c) above comprises testing in vitro one or more substrate, reactant or cofactor at more than one concentration to monitor and optimize methane production in a culture system comprising at least one microorganism isolated from said hydrocarbon-bearing formation, further wherein said culture system provides coal as the sole carbon source.

In one preferred embodiment, at least one microorganism is a bacterial species or an archaeal species capable of converting a hydrocarbon to a product selected from the group consisting of hydrogen, carbon dioxide, acetate, formate, methanol, methylamine, and a methanogenic substrate; a hydrocarbon-degrading bacterial species, a methanogenic bacterial species or a methanogenic archaeal species. In another preferred embodiment, this microorganism is a species of bacteria selected from the genus group consisting of *Pseudomonas, Arcobacter, Desulfuromonas, Pelobacter, Desulfovibrio, Spirochaeta, Erysipelothrix, Thauera, Clostridium, Acholeplasma, Magnetospirillum*, and *Sulfurospirillum*; or a species of archaea selected from the group consisting of *Methanolobus, Methanocalculus*, and members of the phylum Crenarcheaota.

In an alternative embodiment, step (c) is performed with a defined microbial assemblage that combines a culture of a single strain of microorganism from a hydrocarbon-bearing formation with at least one other defined culture of another single strain of microorganism, such that members of said defined microbial assemblage act synergistically to produce methane; and further wherein said culture system provides coal as the sole carbon source. A preferred defined microbial assemblage comprises at least two species of microorganisms selected from the genus group consisting of *Pseudomonas, Arcobacter, Desulfuromonas, Pelobacter, Desulfovibrio, Spirochaeta, Erysipelothrix, Thauera, Clostridium, Acholeplasma, Magnetospirillum, Sulfurospirillum; Methanolobus, Methanocalculus*, and members of the phylum Crenarcheaota.

In various embodiments, the hydrocarbon-bearing formation is selected from the group consisting of coal, peat, lignite, oil shale, oil formation, traditional black oil, viscous oil, oil sands and tar sands. In a preferred embodiment, the formation is coal in a coal seam or coalbed.

In various embodiments, the enzyme involved in the conversion of hydrocarbon to methane is selected from the group consisting of peroxidases, phenol oxidases, alcohol oxidases, laccases, hydrolases, glycosyl hydrolases, esterases, etherases, oxidases, nitrogenases, cellulases, amylases, glucanaeses, pullanases, reductases, dismutases, oxygenases, monooxygenases, dioxygenases, catalases, hydrogenases, and carboxylases. In a preferred embodiment the enzyme is selected from the group consisting of oxygenases, monooxygenases, and dioxygenases.

In various embodiments, the substrate, reactant or co-factor is selected from the group consisting of a sulfur-containing compound, a nitrogen-containing compound, a phosphorous-containing compound, a trace element, an electron acceptor, an electron donor, a halogen, a metal, an alcohol, an organic acid, an alkane, an alkene, an alkyne, an aromatic compound, an amine, an ether, an aldehyde, a ketone, a thiol, acetate, an aromatic hydrocarbon, and a gas. In a preferred embodiment the reactant is oxygen.

In a second aspect, the invention provides processes for enhancing biogenic production of methane in a hydrocarbon-bearing formation, said method comprising introducing a stimulant identified by any of the foregoing methods of the first aspect, into a hydrocarbon-bearing formation.

In one embodiment, the process introduces oxygen into said hydrocarbon-bearing formation. In a preferred embodiment, the hydrocarbon-bearing formation is coal.

In a third aspect, the invention provides processes for enhancing biogenic production of methane in a hydrocarbon-bearing formation, said method comprising modulating an enzyme selected from the group consisting of peroxidases, phenol oxidases, alcohol oxidases, laccases, hydrolases, glycosyl hydrolases, esterases, etherases, oxidases, nitrogenases, cellulases, amylases, glucanaeses, pullanases, reductases, dismutases, oxygenases, monooxygenases, dioxygenases, catalases, hydrogenases, and carboxylases.

In alternative embodiments the enzyme is present in an existing microorganism in the hydrocarbon-bearing formation, or is introduced into the hydrocarbon-bearing formation. In the later embodiment, the enzyme is introduced by introducing a microorganism expressing said enzyme into said hydrocarbon-bearing formation. In one embodiment, the introduced microorganism expressing said enzyme is a recombinant microorganism prepared by modifying a microorganism derived from said hydrocarbon-bearing formation. In another embodiment, the microorganism expressing said enzyme is a synthetic microorganism.

In a fourth aspect, the invention provides methods of identifying a defined microbial assemblage for the conversion of coal to methane that comprises: (a) obtaining a nucleic acid sequence from one or more microorganisms derived from a coal environment; (b) determining the presence of one or more gene product of said nucleic acid sequence, wherein said gene product is an enzyme in a pathway involved in the conversion of coal to methane; (c) preparing a culture of a single strain of said one or more microorganisms from said coal environment, wherein the single strain of microorganism contains said one or more gene product; and (d) combining said cultured single strain of microorganism with at least one other defined culture of another single strain of microorganism to provide a defined microbial assemblage; wherein members of said defined microbial assemblage act synergistically to produce methane.

In one embodiment, there is provided a defined microbial assemblage for the conversion of coal to methane identified by the above invention methods.

In another embodiment, the method further comprises (e) providing a substrate, reactant or co-factor to said defined microbial assemblage that increases methane production.

In preferred embodiments, the defined microbial assemblage comprises at least two species of microorganisms selected from the genus group consisting of *Pseudomonas, Arcobacter, Desulfuromonas, Pelobacter, Desulfovibrio, Spirochaeta, Erysipelothrix, Thauera, Clostridium, Acholeplasma, Magnetospirillum, Sulfurospirillum; Methanolobus, Methanocalculus*, and members of the phylum Crenarcheaota.

In a fifth aspect, the invention provides processes for enhancing biogenic production of methane from coal by introducing a defined microbial assemblage identified by the invention methods described herein into a coalbed.

In a preferred embodiment, such processes comprise introducing a defined microbial assemblage identified as above into a coalbed together with said substrate, reactant or co-factor.

DETAILED DESCRIPTION OF THE INVENTION

Figure 1:
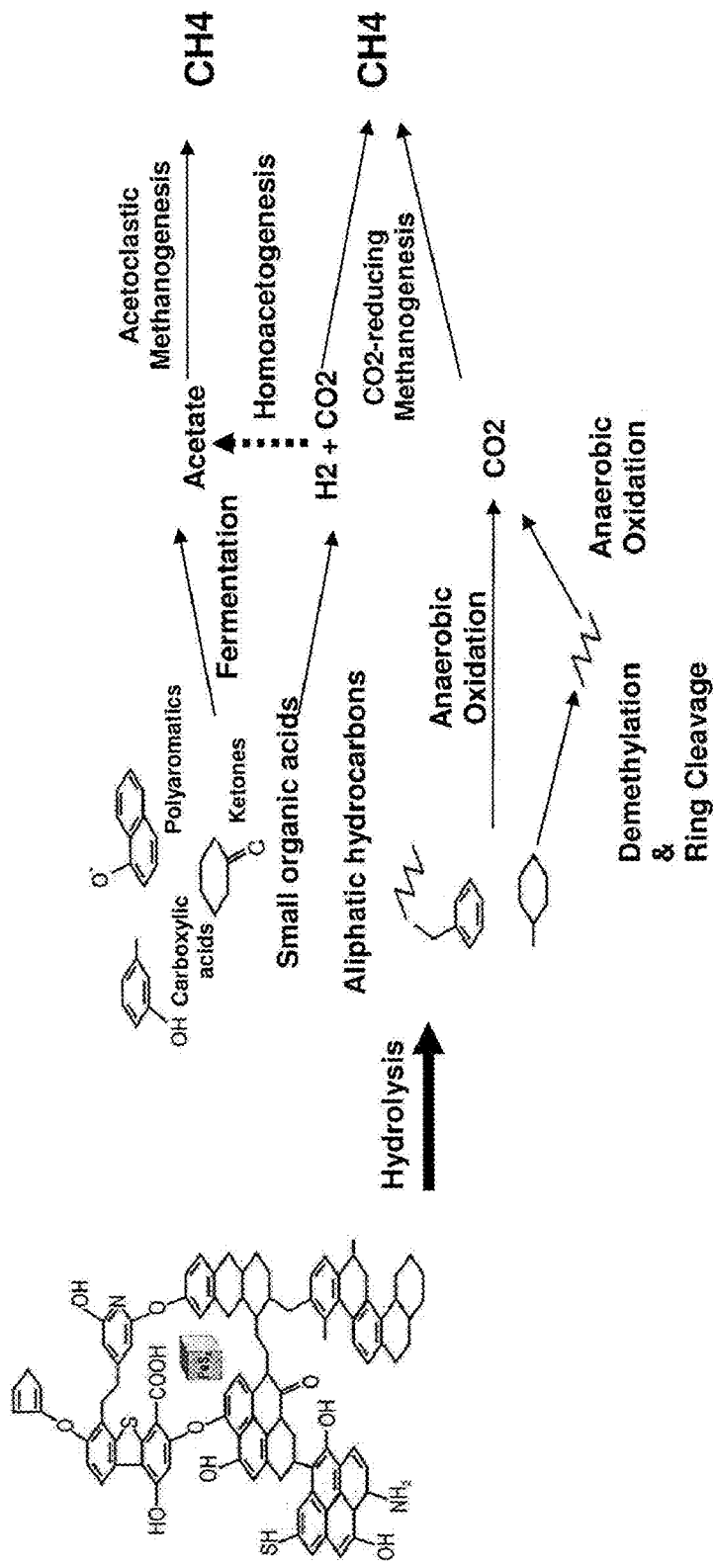
FIG. 1 illustrates a variety of potential enzymatic pathways in the conversion of coal to methane.

The present invention provides novel methods and processes to stimulate biogenic methane production in hydrocarbon-bearing formation, such as coal seams and coalbed methane wells, by using cultivated microorganisms derived from the formation. Genomic information obtained from resident microbial populations residing in the hydrocarbon-bearing formation is used to identify and stimulate enzymes involved in various pathways involved in the conversion of a hydrocarbon to methane, which are present in one or more microorganisms in the formation or introduced into the formation, preferably together with the identified stimulant.

The methods of the present invention provide a stepwise approach to the identification of stimulants and/or DMAs useful for increasing biogenic production of methane. The examples provided herein demonstrate the stepwise approach in the successful identification of stimulants to increase methane production. Briefly, in the examples provided herein, formation water samples were collected from a coalbed methane well in the San Juan Basin, where previous studies indicated an age of 70 million years resulting from an isolation from the surface and no evidence of subsurface mixing events. The water could be collected from the well head, the separation tank (knock out drum) or reservoir tank as these water samples are the most readily available materials. The water samples containing living microorganisms were then visualized via light microscopy, and microorganisms were cultivated using formation water as mineral base. Cultures of microorganisms were enriched for methane-producing microbes using coal as sole carbon source. Various combinations of electron acceptors, such as nitrate, sulfate, or iron-phosphate were tested as stimulants for microbial respiration. The microbial enrichments were then screened for methane production using gas chromatography. The cultivated microbial community composition was analyzed using phylogenetic markers to identify the dominant microbial groups and several microorganisms were independently cultured into pure cultures (deconvolution) to study their enzymatic profiles, metabolism and capacity to degrade coal. The community may be reconstructed and formulated for optimized methane production from coal in a rational fashion (reconstitution) creating a designed complex microbial ecosystem or defined microbial assemblage (DMA).

The power of the methods of the present invention can be seen in the identification of oxygen as a stimulant in that increases the biogenic production of methane from coal. By identifying the presence of a large number of oxygenases, monooxygenases, and dioxygenases in the genomic analyses of the samples, oxygen was identified as a stimulant. The identification of these enzymes was unexpected due to the anaerobic environment from which the microorganisms were derived. Bacterial aromatic hydrocarbon dioxygenases are multicomponent enzyme systems that add dioxygen to the aromatic nucleus to form arene cis-diols, for the oxidation of benzene to cis-1,2-dihydroxycyclohexa-3,5-diene (benzene cis-diol) by toluene dioxygenase (Gibson, D. T., Cardini, G. E., Maseles, F. C., Kallio, R. E. Incorporation of oxygen-18 into benzene by *Pseudomonas putida*. Biochemistry. 1970. 9:1631-1635). Other types of oxygenases detected in the genomic analysis, methane-producing enrichment and the isolated *Pseudomonas* strain are related to catechol 2,3-dioxygenase. Catechol dioxygenases are metalloprotein enzymes that carry out the oxidative cleavage of catechols. This class of enzymes incorporates dioxygen into the substrate. Catechol dioxygenases belong to the class of oxidoreductases and have several different substrate specificities, including catechol 1,2-dioxygenase (EC 1.13.11.1), catechol 2,3-dioxygenase (EC 1.13.11.2), and protocatechuate 3,4-dioxygenase (EC 1.13.11.3). The active site of catechol dioxygenases most frequently contains iron, but manganese-containing forms are also known. The reactions catalyzed by the oxygenases will release energy that can be used for microbial growth, and as a result of such growth other metabolites would be produced which can be assimilated by other species.

Oxygen may be a relevant gas in the subsurface as aerobic strains have been reported to be thriving in supposed anaerobic environments such as oil deposits (Nazina et al. The phylogenetic diversity of aerobic organotrophic bacteria from the Dagang high temperature oil field. 2007. Microbiology 74:343-351). However, those methods do not describe a mechanism or mode of action, and the ability to regulate or control the underlying biological processes and microbial communities responding to such stimuli are limited without such knowledge.

Sources of Microorganisms and Their Characterization

As used herein, the term "hydrocarbon-bearing formation" refers to any hydrocarbon source from which methane can be produced, including, but not limited to, coal, peat, lignite, oil shale, oil formation, traditional black oil, viscous oil, oil sands and tar sands. In the various embodiments discussed herein, a hydrocarbon-bearing formation or even a hydrocarbon-bearing formation environment may include, but is not limited to, oil shale, coal, coal seam, waste coal, coal derivatives, lignite, peat, oil formations, tar sands, hydrocarbon-contaminated soil, petroleum sludge, drill cuttings, and the like and may even include those conditions or even surroundings in addition to oil shale, coal, coal seam, waste coal, coal derivatives, lignite, peat, oil formations, tar sands, hydrocarbon-contaminated soil, petroleum sludge, drill cuttings, and the like. In some embodiments, the present invention may provide an in situ hydrocarbon-bearing formation sometimes referred as an in situ hydrocarbon-bearing formation environment or in situ methane production environment. Embodiments may include an ex situ hydrocarbon-bearing formation sometimes referred to as an ex situ hydrocarbon-bearing formation environment or an ex situ methane production environment. In situ may refer to a formation or environment of which hydrocarbon-bearing sources may be in their original source locations, for example, in situ environments may include a subterranean formation. Ex situ may refer to formations or environments where a hydrocarbon-bearing formation has been removed from its original location and may perhaps even exist in a bioreactor, ex situ reactor, pit, above ground structures, and the like situations. As a non-limiting example, a bioreactor may refer to any device or system that supports a biologically active environment.

Using coal as an exemplary hydrocarbon-bearing formation, there are numerous sources of indigenous microorganisms that may be playing a role in the hydrocarbon to methane conversion that can be analyzed. Coal is a complex organic substance that is comprised of several groups of macerals, or major organic matter types, which accumulate in different types of depositional settings such as peat swamps or marshes. Maceral composition, and therefore coal composition, changes laterally and vertically within individual coal beds. Once microorganisms are identified as containing an enzyme in a pathway involved in a conversion step, different defined microbial assemblages or stimulants identified by the methods of the present invention may work better on specific maceral groups and therefore, each coal bed may be unique in what types of microorganism and stimulant are most efficient at the in situ bioconversion of the coal.

There are numerous naturally occurring microbes that are associated with coal and other organic-rich sediments in the subsurface. Over time, these microbial species may have become very efficient at metabolizing organic matter in the subsurface through the process of natural selection. The relatively quick adaption of bacteria to local environmental conditions suggests that microorganisms collected from basins, or individual coal seams, may be genetically unique. Once collected, these microorganisms can be grown in laboratory cultures as described herein to evaluate and determine factors enhancing and/or limiting the conversion of coal into methane. In some cases, a key nutrient or trace element may be missing, and addition of this limiting factor may significantly increase methane production. When bacteria are deprived of nutrients, physiological changes occur, and if the state of starvation continues, all metabolic systems cease to function and the bacteria undergo metabolic arrest. When environmental conditions change, the bacteria may recover and establish a viable population again. Therefore, it is possible that some bacteria in organic-rich sediments have reached a state of metabolic arrest and the addition of nutrients is all that is required to activate the population under the present invention. By specifically analyzing the enzymes present in such populations, we can identify ways to stimulate metabolic pathways involved in the conversion of coal to methane that are being carried out by one or more members of these microbial populations.

Anaerobic bacteria from the subsurface can be collected by several different methods that include (1) produced or sampled formation water, (2) drill cuttings, (3) sidewall core samples (4) whole core-samples, and (5) pressurized whole core samples. Pressurized core samples may present the best opportunity to collect viable microbial populations, but we have found collection of microbial populations from formation waters has provided a representative sample of the microbial populations present. Methanogens are obligate anaerobes, but can remain viable in the presence of oxygen for as much as 24 hours by forming multicellular lumps. Additionally, anoxic/reducing microenvironments in an oxygenated system can potentially extend anaerobic bacterial viability longer. In some cases, drill cuttings collected and placed in anaerobic sealed containers will contain microorganisms that are capable of converting the coal to methane within a few hours, thereby giving erroneous gas content measurements.

We have optimized methods of on-site collection to provide optimal recovery of anaerobic populations of microorganisms therein. The present invention involves the collection of microbial populations anaerobically with methods previously described by PCT Application No. PCT/US2008/057919 (WO2008/116187), and the cultivation of indigenous microorganisms residing in the hydrocarbon-bearing formation environment, such formation water or coalbed methane wells.

The methods provided herein also afford the opportunity for genetically altering microorganisms. By identifying enzymatic functions within resident microorganisms, and stimulants that may be used to increase methane production, we can use this information to genetically engineer microorganisms to have abilities that can be tied to stimulation and increased methane production. Selections of microorganisms by the methods described herein enrich for the ability to efficiently metabolize coal and other organic-rich substrates. Once the enzymatic analyses are performed on these enriched cultures, we can optimize targeted stimulants and/or genetically-engineered bacteria. Various possibilities to enhance methane production from wells comprise introducing stimulants identified, microorganisms identified, defined assemblages of organisms, genetically-modified organisms, or any combinations thereof into the formation.

According to the methods of the present invention, indigenous microorganisms are identified and then stimulated to transform hydrocarbons to methane. Microorganisms naturally present in the formation are preferred because it is known that they are capable of surviving and thriving in the formation environment, and should provide enzymatic components of various pathways proceeding from hydrocarbon hydrolysis through to methanogenesis. However, this invention is not limited to use of indigenous microorganisms. When analyzing enzymatic profiles of indigenous microorganisms, it may be advantageous to combine such information with that of exogenous microorganisms. This information may come from known microorganisms, preferably those that are suitable for growing in the subterranean formation, and by analogy, have similar potential enzymatic processes.

The term "defined microbial assemblage" or "DMA" as used herein, refers to a culture of more than one microorganism, wherein different strains are intentionally combined or selected to optimize the conversion of a hydrocarbon to methane. The microorganisms of the assemblage are "defined" such that at any point in time we can determine the members of the population by use of genetic methods, such as 16S taxonomy as described herein. The DMA does not necessarily remain static over time, but may evolve as cultures flux to optimize hydrocarbon hydrolysis and methane production. Optimally, the DMA is prepared to provide microorganisms harboring strong enzymatic profiles in the hydrocarbon to methane pathways. The DMA may consist of 2 or more microorganisms, in any combinations to provide bacterial or archael species capable of converting a hydrocarbon to any intermediate leading to the production of methane, and/or any methanogenic species. For example, there may be 2, 3, 4, 5, 6, 7, 8, 9, 10, 11, 12, 13, 14, 15 or more organisms present in the DMA. The members of the DMA act synergistically to produce methane, amongst themselves, or together with microorganisms present in the hydrocarbon-bearing formation.

The term "microorganism" is intended to include bacteria and archaea organisms, as well as related fungi, yeasts and molds. It will be understood that bacteria and archaea are representative of microorganisms in general that can degrade hydrocarbons and convert the resulting products to methane. The dividing lines between classes of microorganisms are not always distinct, particularly between bacteria and fungi. It is preferred, therefore, to use the term microorganisms to include all microorganisms that can convert hydrocarbons to methane, whatever the commonly used classifications might be. Of these microorganisms, those usually classified as bacteria and archaea are, however, preferred. If exogenous bacteria and archaea are used in the methods described herein, other microorganisms such as fungi, yeasts, molds, and the like can also be used.

The term "anaerobic microorganism" as used herein, refers to microorganisms that can live and grow in an atmosphere having less free oxygen than tropospheric air (i.e., less than about 18%, by mol., of free oxygen). Anaerobic microorganisms include organisms that can function in atmospheres where the free oxygen concentration is less than about 10% by mol., or less than about 5% by mol., or less than about 2% by mol., or less than about 0.5% by mol.

The term "facultative anaerobes" as used herein, refers to microorganisms that can metabolize or grow in environments with either high or low concentrations of free oxygen.

The conversion of hydrocarbons to methane requires the active participation of methanogens. A "methanogen" as used herein, refers to obligate and facultative anaerobic microorganisms that produce methane from a metabolic process. The presence of methanogens within the samples indicates the high likelihood of in situ methane formation. Methanogens are typically classified into four major groups of microorganisms: *Methanobacteriales, Methanomicrobacteria* and relatives, *Methanopyrales* and *Methanococcales*. All methanogenic microorganisms are believed to employ elements of the same biochemistry to synthesize methane. Methanogenesis is accomplished by a series of chemical reactions catalyzed by metal-containing enzymes. One pathway is to reduce $CO_2$ to $CH_4$ by adding one hydrogen atom at a time ($CO_2$-reducing methanogenesis). Another pathway is the fermentation of acetate and single-carbon compounds (other than methane) to methane (acetate fermentation, or acetoclastic methanogenesis). The last step in all known pathways of methanogenesis is the reduction of a methyl group to methane using an enzyme known as methyl reductase. As the presence of methyl reductase is common to all methanogens; it is a definitive character of methanogenic microorganisms. The preferred method for identifying the presence of methanogens is to test directly for the methanogen gene required to produce the methyl reductase enzyme. Alternatively the presence of methanogens can be determined by comparison of the recovered 16S rDNA against an archaeal 16S rDNA library using techniques known to one skilled in the art (generally referred to herein as 16S taxonomy).

Classes of methanogens include *Methanobacteriales, Methanomicrobacteria, Methanopyrales, Methanococcales,* and *Methanosaeta* (e.g., *Methanosaeta thermophila*), among others. Specific examples of methanogens include *Methanobacter thermoautotorophicus,* and *Methanobacter wolfeii*. Methanogens may also produce methane through metabolic conversion of alcohols (e.g., methanol), amines (e.g., methylamines), thiols (e.g., methanethiol), and/or sulfides (e.g., dimethyl sulfide). Examples of these methanogens include methanogens from the genera *Methanosarcina* (e.g., *Methanosarcina barkeri, Methanosarcina thermophila, Methanosarcina siciliae, Methanosarcina acidovorans, Methanosarcina mazeii, Methanosarcinafrisius*); *Methanolobus* (e.g., *Methanolobus bombavensis, Methanolobus tindarius, Methanolobus vulcani, Methanolobus taylorii, Methanolobus oregonensis*); *Methanohalophilus* (e.g., *Methanohalophilus mahii, Methanohalophilus euhalobius*); *Methanococcoides* (e.g., *Methanococcoides methylutens, Methanococcoides burtonii*); and/or *Methanosalsus* (e.g., *Methanosalsus zhilinaeae*). They may also be methanogens from the genus *Methanosphaera* (e.g., *Methanosphaera stadtmanae* and *Methanosphaera cuniculi*, which are shown to metabolize methanol to methane). They may further be methanogens from the genus *Methanomethylovorans* (e.g., *Methanomethylovorans hollandica*, which is shown to metabolize methanol, dimethyl sulfide, methanethiol, monomethylamine, dimethylamine, and trimethylamine into methane).

As described herein, it is a feature of the present invention that microbial communities obtained from a variety of environmental samples are amenable to study using genomic tools as provided herein; in addition, microbial populations can be cultivated and optionally isolated and/or enriched in the laboratory using invention methods. By applying these approaches at the genomic level, and by specifically characterizing the enzymatic profiles of microorganisms involved in the conversion of hydrocarbons to methane, it is possible to develop a fundamental understanding of the metabolism of the microbial communities and, more specifically, the methanogenic degradation of coal in the formation water and coal seams. As such, we are then able to elucidate the ecological niche of each population and ultimately develop stimulants and/or DMAs that could yield an enhancement in the biological methane production.

According to the methods of the present invention microorganisms present in the hydrocarbon-bearing formation environment (indigenous microorganisms), and/or enzymes present in such microorganisms are identified and then stimulated or modulated to transform hydrocarbons to methane. Microorganisms naturally present in the formation are preferred because it is known that they are capable of surviving and thriving in the formation environment. However, this invention is not limited to use of indigenous microorganisms. Exogenous microorganisms suitable for growing in the subterranean formation may be identified, or enzymes therefrom identified, and such microorganisms or enzymes introduced into the formation by known injection techniques before, during, or after practicing the process of this invention. For example, if the formation contains only two microorganisms of a desired three-component consortia, or only two of three desired enzyme functions for the enzymatic pathway from hydrocarbon to methane, then the missing microorganisms, enzyme, or a stimulant for such a microorganisms or enzyme could be injected into the formation. Microorganism, indigenous or exogenous, may also be recombinantly modified or synthetic organisms.

Metagenomic and Nucleic Acid Analyses

In the present invention a new approach and potentially a paradigm for enhanced methane production is proposed. This involves the description of the genomes and metagenomes, the most fundamental biological entities in nature. By characterizing the total community genome, also known as metagenome, in methane production sites it is possible to gain a fundamental understanding of the microbial methane production including utilized substrates and generated intermediates and products. Furthermore, the interactions and synergistic effects among different populations through an electron transfer that ultimately results in an energy cascading directed to methane can be elucidated. The cultivation data in combination with the genomic results suggest that microbial populations and hence gas production in the subsurface can be stimulated by an intervention consisting of supplemented substrates, reactants or growth factors and/or specific microbial inoculations which result in an increased methane production. The methods of the present invention and the results obtained therefrom represent the first study in the subsurface microbiology integrating metagenomics, microbial cultivation, and genome analysis of the isolated strains. The results demonstrate the interdependence of these disciplines is necessary in order to develop a comprehensive ecosystem understanding.

The term "metagenome" or "metagenomics" as used herein, refers to the genetic material, and analysis of this genetic material, from environmental samples, representing the profile of all microorganisms present in the sample. Metagenomics is also referred in the art as "community genomics" or "environmental genomics". Typically, metagenomics comprises the nucleic acid sequencing and analysis of total DNA of the population of organisms recovered from an environment, for example, a pooled DNA recovery from all microorganisms in a sample without the need for culturing strains of individual members of the microbial population themselves.

Generally, the DNA from the entire microbial community, i.e., the metagenome, is first isolated and then amplified using gene-specific primers (commonly 16S universal primers) and PCR technology. Next, the fragments are purified by a number of techniques and then ligated into molecular vehicles (for example, plasmid DNA) and transformed into bacteria (usually E. coli) as part of the cloning process to create large numbers of isolated DNA fragments. Cultures of individual bacterial colonies are used to isolate individual clones (recombinant plasmid DNA) and then these clones are sequenced using target specific primers. The resultant DNA sequences are then compared with known strains of DNA sequences in molecular gene databases. In most cases, the identities of the microorganisms can be inferred if there are close matches to known microorganisms having known physiological and ecological characteristics.

Typically, DNA is isolated by any methods known in the art from environmental DNA and then sheared into fragments that are used in construction of a DNA clone library. Clone libraries may be either small or medium insert (2-15 kb insert size) libraries or large insert bacterial artificial chromosome (BAC) or fosmid libraries (up to 150 kb insert size), that may be sequenced in either a random or targeted fashion.

Further analyses of the metagenome comprises cultureindependent 16S rRNA analysis to determine phylogenetic diversity (referred to as 16S taxonomy), and further sequence analysis to identify genes of interest in the metagone. In a random sequencing approach, clones are randomly chosen and end-sequenced, and the resulting sequences are assembled into larger contiguous pieces ("contigs") by matching up overlapping sequences. The resulting data are contigs of different lengths as well as shorter unassembled fragments. The availability of completely sequenced "reference" genomes may assist in the assembly process for closely related genomes. In the absence of this, contigs may be assigned to various "bins" based on their G+C content, codon usage, sequence coverage, presence of short n-mers (nucleotide frequency), and other parameters, allowing them to be sorted into groups that can be viewed as a "species". Coding sequences (CDSs, genes) are then predicted from these sequence data using various methods. Often in the random sequencing approach, identified genes may not be attributable to a particular microbial species (i.e., there is no taxonomic or phylogenetic affiliation), these nonetheless represent abilities of the general microbial community and may reveal characteristics of their environment. In a "targeted" sequencing approach, clones are first screened for the presence of a desirable gene (e.g., by PCR amplification) or a gene function (by functional assay). Sequencing targeted large-insert clones in their entirety allows the possibility of recovering complete operons, e.g., those encoding metabolic pathways.

A common approach is to target fosmids bearing phylogenetically informative genes such as 16S rRNA. In this method, known as "phylogenetic anchoring", if a 16S rRNA gene is detected, the fosmid insert is sequenced in its entirety, allowing us to assign the genomic DNA sequence to a specific phylotype. This approach helps affiliate phylogeny (rRNA) with putative functional genes (predicted from flanking insert sequences). Fosmids bearing process-specific or biomarker genes (e.g., for processes that may be prominent in the environment under study, like methane oxidation or denitrification) may also be targeted for sequencing in order to expand information on pathways for these processes. By combining both random and targeted approaches, genes of interest (e.g., 16S rRNA genes from unknown phylotypes) or novel genes identified from the random sequencing phase may be used to screen and target other clones for sequencing, or to identify linking clones and expand genome coverage.

In one specific comparative analysis, genes identified from the metagenome and/or microorganisms represented therein can be compared to known protein families to determine the presence of gene products encoding enzymes in pathways involved in the conversion of a hydrocarbon to methane. For example, the Pfam database is a large collection of protein families, each represented by multiple sequence alignments and hidden Markov models (HMMs). Proteins are generally composed of one or more functional regions, commonly termed domains. Different combinations of domains give rise to the diverse range of proteins found in nature. The identification of domains that occur within proteins can therefore provide insights into their function. See, The Pfam protein families database: R. D. Finn, J. Tate, J. Mistry, P. C. Coggill, J. S. Sammut, H. R. Hotz, G. Ceric, K. Forslund, S. R. Eddy, E. L. Sonnhammer and A. Bateman, Nucleic Acids Research (2008) Database Issue 36:D281-D288. By comparing genomic information to the Pfam database, the methods provided herein provide a profile of the enzymatic functions present in the metagenome, individual strains of microorganisms, DMAs, or any combinations thereof.

Identification of Stimulants

The term "stimulant" as used herein refers to any factor that can be used to increase or stimulate the biogenic production of methane in a hydrocarbon-bearing formation. Preferably, the stimulant is a substrate, reactant or co-factor for an enzyme that is involved in a pathway involved in the conversion of a hydrocarbon to methane. In certain cases, the stimulant is added to modulate an enzyme (increase, decrease or modulate by any means) that is present in an existing microorganism in the hydrocarbon-bearing formation. In certain cases, the stimulant may be the enzyme itself, a microorganism (for example, a microorganism expressing an enzyme or another protein to modulate a relevant enzyme, or such a microorganism produced recombinantly or synthetically), or a defined microbial assemblage. In any case, the function of the stimulant is to boost existing production by increasing the level of activity or growth of a microorganism, or to increase, decrease or modulate by an means the enzymatic activity of an enzyme involved in a pathway involved in the conversion of a hydrocarbon to methane in order to optimize the end production of methane from the hydrocarbon-bearing formation.

Stimulants may provide for enhancement, replacement, or addition of any enzyme that is not optimally represented or functional in the hydrocarbon-bearing environment. The goal is to optimize and/or complete of the pathway from hydrocarbon to methane. Generally this requires representation of enzymes, or microorganisms expressing enzymes that are capable of converting a hydrocarbon to a product such as hydrogen, carbon dioxide, acetate, formate, methanol, methylamine or any other methanogenic substrate, and methanogenic enzymes. General categories of enzymes include enzymes capable of low rank coal hydrolysis, coal depolymerization, anaerobic or aerobic degradation of polyaromatic hydrocarbons, homoacetogenesis, and methanogenisis (including hydrogenotrophic or $CO_2$ reducing and acetoclastic), and any combinations thereof to achieve conversion of a hydrocarbon to methane. Enzymes providing such functions may include, for example, peroxidases, phenol oxidases, alcohol oxidases, laccases, hydrolases, glycosyl hydrolases, esterases, etherases, oxidases, nitrogenases, cellulases, amylases, glucanaeses, pullanases, reductases, dismutases, oxygenases, monooxygenases, dioxygenases, catalases, hydrogenases, and carboxylases.

Examples of stimulants include freeze-dried microbes such as methanogens, syntrophs, fermentative and/or hydrolytic microorganism; or the stimulant, substrate, reactant or co-factor may be of chemical nature including such compounds as nitrogen, phosphorus, potassium, vitamins, trace metals, yeast extract, a sulfur-containing compound, a nitrogen-containing compound, a phosphorous-containing compound, a trace element, an electron acceptor, an electron donor, a halogen, a metal, an alcohol, an organic acid, an alkane, an alkene, an alkyne, an aromatic compound, an amine, an ether, an aldehyde, a ketone, a thiol, acetate, an aromatic hydrocarbon, and a gas.

Once an enzyme is identified by a method of the present invention, an appropriate substrate, reactant or co-factor for that enzyme can be identified.

Specific stimulants include, for example, yeast extract, $NH_4Cl$, $NaNO_3$, $K_2HPO_4$, Coenzyme M, $PO_4$, vitamin mix minus phosphate, trace metals, $O_2$, $H_2$, phosphorous compounds, lactic acid, mineral amendments (such as chloride, ammonium, phosphate, sodium, potassium, magnesium and calcium), metal amendments (such as Mn, Fe, Co, Zn, Cu, Ni, Se, W, or Mo), vitamin amendments (such as pyridoxime, thiamine, riboflavin, calcium, pantothenate, thioctia acid, P-amino benzoic acid, nicotinic acid, Vitamin B12, biotin, folic acid and mecaptoheptanesulfonic acid, pyruvate, alkyl alcohols, methanol, ethanol, 2-propanol, 2,3 butanediol, vanillate, glycine, cysteine, formate, ethanolamine, and 3,4, 5-trimethoxybenzoate, water amendment, formate, acetate, lactate, private, NaCL, cellulose, mineral solution, cinnamic acid, benzoic acid, DNG, alasan, fertilizer composition, chitin, chitosan, chlorate, perchlorate, and any combinations thereof.

Incorporation of Stimulants to Increase Methane Production

The methods and processes of the present invention can be readily used for field applications and the enhancement of in situ or ex situ methane production from any hydrocarbon-bearing formation such as coal. There are several methods or combination of injection techniques that are known in the art that can be used in situ. Stimulants, DMAs, or microorganisms identified by the methods of the present invention can be injected directly into the fractures in the formation. Fracture orientation, present day in situ stress direction, reservoir (coal and/or shale) geometry, and local structure are factors to consider. For example, there are two major networks (called cleats) in coal beds, termed the face cleat and butt cleat system. The face cleats are often more laterally continuous and permeable, whereas the butt cleats (which form abutting relationships with the face cleats) are less continuous and permeable. During the stimulation of coal bed methane wells, the induced fractures intersect the primary face cleats that allow greater access to the reservoir. However, when the present day in situ stress direction is perpendicular the face cleats, then stress pressure closes the face cleats thereby reducing permeability, but at the same time in situ pressures increase permeability of the butt cleats system. Under these conditions, induced fractures are perpendicular to the butt cleat direction, providing better access to the natural fracture system in the reservoir. The geometry of the injection and producing wells, and whether or not horizontal cells are used to access the reservoir, depend largely upon local geologic and hydrologic condition.

The objective of hydraulic fracture stimulation of coal bed methane, as in conventional oil and gas wells, is to generate an induced fracture network that connects with the naturally occurring fracture network of the reservoir. Stimulants, DMAs, or microorganisms identified by the methods of the present invention can be introduced into the naturally-occurring and artificially-induced fractures under pressure to drive the mixture into naturally-occurring fractures deep into the reservoir to maximize bioconversion rates and efficiency. During fracture stimulation of reservoirs, sand propant and various chemicals may be pumped into the formation under high pressure through a drill rig.

Stimulants, DMAs, or microorganisms may be injected into the reservoir at the same time as fracture stimulation and/or after the hydraulic fractures are generated. Most in situ microbial applications are expected to occur after fracture stimulation and removal of completion fluids when subsurface anaerobic conditions are reestablished. However, under simultaneous in situ microbial and fracture stimulation, the use of stimulation fluids under anoxic or suboxic conditions is preferred so that anaerobic conditions in the reservoir are maintained, or can be readily attained after stimulation. The injection of aerobic bacteria during simultaneous stimulation would result in the rapid consumption of oxygen and return to anaerobic conditions.

In some cases, pretreatment fluids that modify the coal, carbonaceous shale, or organic-rich shale for bioconversion may be used with the fracture fluids. However, the preferred method for encouraging in situ bioconversion of organic matter is to inject stimulants, DMAs, or microorganisms under pressure and anaerobic conditions after hydraulic fracture stimulation and subsequent flushing of the well.

Figure 16:
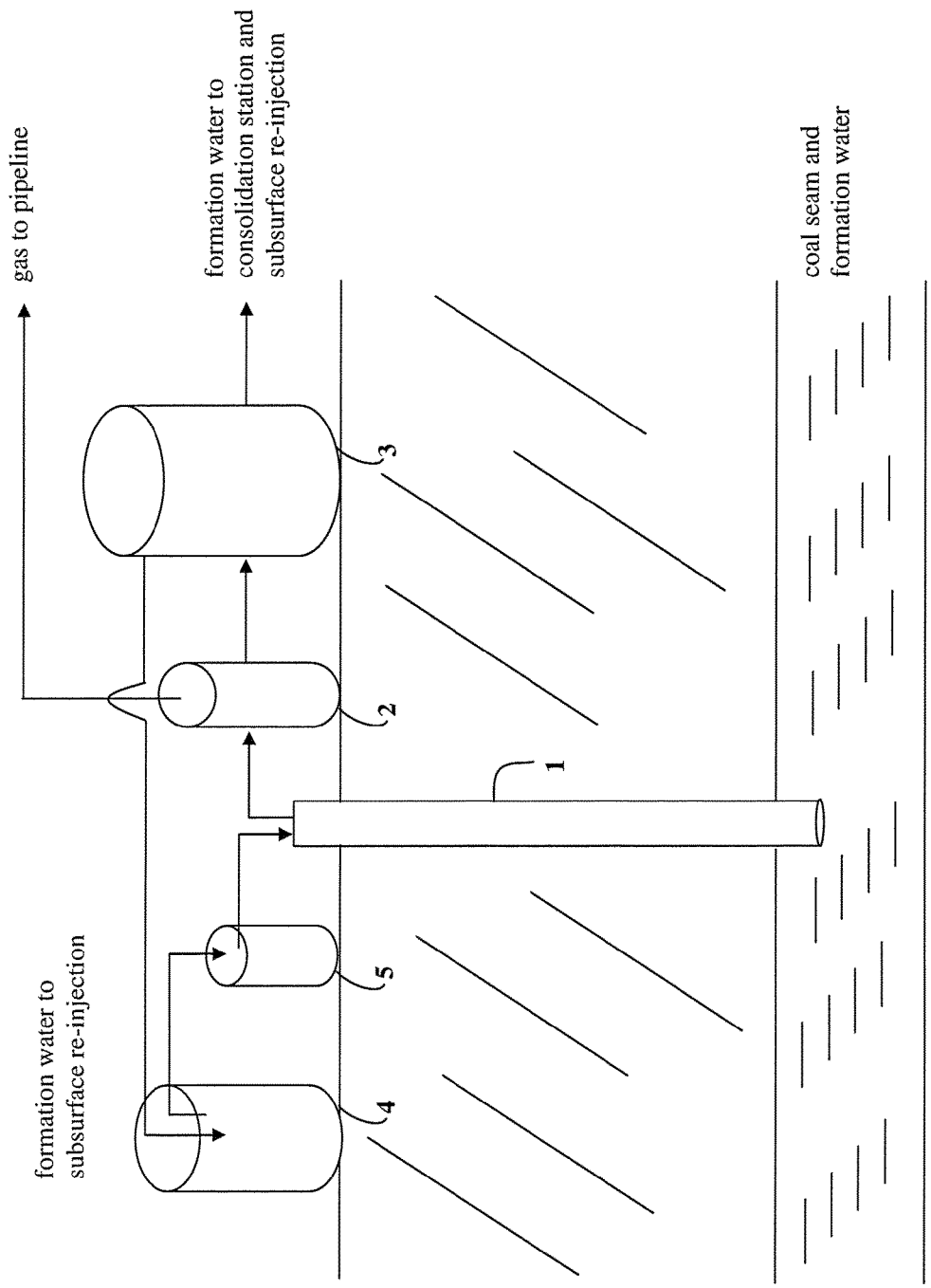
FIG. 16 illustrates a process for introducing an external factor such as an enzyme or stimulant to a coalbed via re-injected formation water to increase methane production.

Stimulants, DMAs, or microorganisms identified by the methods of the present invention may be introduced by re-introduction of the formation water to the subsurface as depicted in FIG. 16. Briefly, methane and formation water are pumped from the well casing 1 into the separation tank 2 (also known as the knock out drum) to remove the gas from the water. The formation water is stored in the reservoir tank 3, from which it can be forwarded to a consolidation station or directed for re-injection to the subsurface. Stimulants, DMAs, or microorganisms can then be added to the preparation tank 4 and mixed with the recovered formation water. A compressor 5 or pressurized system can then be used to introduce the stimulants, DMAs, or microorganisms in the formation water to the subsurface.

In situ dissolved oxygen present in the formation waters may not be accessible to microorganisms in the coal seams and thus becomes a limiting factor for enhanced methane production. The introduction of stimulants, DMAs, or microorganisms, or the delivery of gases, liquids, gels or solids can provide an environment suitable for enhanced methane, including strains capable of aerobic degradation of hydrocarbons bundled with oxygen. For example, in an exemplary embodiment an inoculum composed of the suitable indigenous strains such as *Pseudomonas* at a cell number of $10^7$ cells per ml can be mixed with a gel composed of organic substrates such as glycerol than can be used as nutrients stimulating growth through fermentation and secretion of metabolites including hydrogen that can be used by methanogens. Once the gel has been assimilated, it will slowly release the optimal amounts of oxygen that in turn will be used by the strains with the capacity for aerobic hydrocarbon degradation. These amendments and resulting metabolism will stimulate the electron flow to methane producing a higher amount and yield compared to control wells in the same seam that are not intervened. This is particularly advantageous for strains with the capacity to grow aerobically or anaerobically and can adapt their metabolism for hydrocarbon degradation. In a separate embodiment, formation water with a high concentration of dissolved oxygen is injected in a well in order to dispense some of the oxygen needed for the oxygenase-catalyzed reactions. Oxygen can be dissolved in formation water by aerating with mechanical systems such as impellers or other mechanisms. Alternatively, an intermediate mechanism can be used to introduce oxygen to the anaerobic environment. For example, chlorate can be used as an electron acceptor to generate oxygen release by the enzymes chlorate reductase and chlorite dismutase, which were both present in the metagenomic analyses.

In an alternative embodiment, a particle-based method can be used to distribute stimulants, DMAs, or microorganisms (collectively, the intervention agents) during the fracing process. The goal is to introduce these interventions in order to produce a sustainable enhancement of methane production. An improved delivery system injects the agents deep into the well fissures and enables a time-released deployment. For example, the well intervention agent may be formulated as either a time-released coating over the sand grains used in the fracing process or as hard particles which slowly dissolve with time; the size is envisioned as roughly the same as the sand grains used in the fracing process, and could be mixed together before added to the guar gum solution known as the propant. In either format, once the propant and particles are pumped into the well and pressured, the coated sand grains or hard particles mixed with the sand are pressure-injected in the well fractures, keeping them open to facilitate gas or oil release. Since the intervention agents are formulated in a time-release manner not dissimilar to some pharmaceutical agents, the compounds and/or microbes would dissolve slowly and diffuse into the surrounding formation water and into the coal cleats (or fine rock cracks in the case of oil) where adhered bacteria presumably reside. In this fashion, the dissolving agents continuously stimulate the biogenic conversion of coal to methane. The formulations could be fashioned to release the intervention agent over a period of hours, days, weeks or months in order to optimize the methane stimulation process. The coatings or particles could be prepared in the absence of oxygen in order to maintain the viability of strict anaerobic microbes, or they could also harbor gases which stimulate methane production.

The following examples are offered to illustrate, but not limit, the invention.

Example 1

Sampling and Enrichment of Methane-Producing Microorganisms from Coalbed Methane Well A volume of 200 L of formation water was collected from the reservoir tank and a volume of 20 L from the separation tank in a coalbed methane well located in the San Juan Basin, Colo., USA. The water samples were then filtered with a series of sterile sieves from 1 mm to 45 μm to remove large pieces of coal and oils that came with the formation water. A subsample was then transferred into a 1 L sterile bottle and sparged with $N_2$ using a portable tank and a glass pipette. The bottles were then sealed with a butyl stopper and used for inoculations.

The media consisted of a mineral base and crude coal as carbon source dispensed into Hungate tubes with 5 ml of culture and 0.5 g of coal as sole carbon source.

Medium composition for methanogenic enrichments and pure cultures:

Per 1 L of sterile produced water:
$NH_4Cl$ 0.5 g
$KH_2PO_4$ 0.75 g
$K_2HPO_4$ 1.5 g
commercial (ATCC) vitamin and trace element solution 10 mL of each
Sterilized at 1 atm for 15-30 minutes, and then added from the stock solution:
yeast extract 0.05% final concentration
$Na_2S\cdot 9H_2O$ 3 mM final concentration cysteine-HCl 3 mM final concentration Sterilized at 1 atm for 15-30 minutes, and then added from the stock solution:

appropriate carbon and energy source for methanogenesis: gas mix $CO_2:H_2/20:80$ up to 2 atm In some cultures, a mix of electron acceptors consisting of sodium nitrate (10 mM), sodium sulfate (10 mM) and iron phosphate (10 mM) were used to stimulate anaerobic respiration and growth. The media was prepared anaerobically by dispensing all components in an anaerobic chamber with an atmosphere of 5% $H_2$, 5% $CO_2$ and balanced with $N_2$. Other cultures included the use of autoclaved coal. No reducing agents such as sodium sulfide or cysteine were used in the media preparation. The samples were inoculated directly in the field by collecting 1 ml anaerobically from the 1 L sample bottles with a syringe and a needle that was previously flushed three times with $N_2$. The inoculated tubes were incubated at 30° C. and transported to the lab. After a few weeks of growth, the samples were monitored for growth microscopically and methane production was measured by gas chromatography. The enrichments were selected for their ability to grow on coal as sole carbon source and their production of methane. The highest methane concentration was detected in the cultures where electron acceptors were omitted. After six consecutive transfers of the primary enrichment, methane production appeared to be reproducible and scalable consistently resulting in 3% of the head space. The community selected for ongoing characterization was subsequently transferred into serum bottles and methane was produced consistently at about 3% in the headspace between 10 and 30 days at 30° C.

Example 2

Characterization of Community of Microorganisms from Coalbed Methane Well and the Enrichment Methane-Producing Microorganisms Total community DNA was extracted from the formation water samples with methods optimized to efficiently separate nucleic acids from coal present in the formation waters and enrichments. Genomic libraries were constructed from the reservoir tank water sample using multiple methods to assess potential biases and to efficiently capture the total microbial populations including bacteria, archaea and eukarya. Previous genomic analyses on the reservoir tank revealed a relative low complexity compared to environments such as soils or surface sea water. Notably, the absence of eukaryotic cells was striking. There were two dominant cell lineages in the genomic data corresponding to the Proteobacteria, Arcobacter and Chrysiogenes whose genomes can be re-assembled from the community DNA. Their metabolism may be associated to the degradation of oils and other hydrocarbons and the respiration of arsenites.

Preparation of DNA

The water sieved to a size less than 45 μm was then filtered using a series of membranes with pore sizes of 3, 0.8 and 0.1 μm connected in series. The membranes were collected from the filter apparatus, frozen with Tris-EDTA buffer at −20° C. and transported to the lab. DNA was extracted from the membranes as follows.

The filters were bathed for 45 minutes at room temperature on a rotating wheel in an excess volume of lysis buffer (50 mM NaCl, 50 mM Tris pH 8.0, 50 mM EDTA, 5% SDS, 4% polyvinylpyrrolidone, 1% polyethylene glycol (8000), 0.5 M glucose, 200 mM beta-mercaptoethanol, 10 mM spermidine, 10 mM ascorbic acid, 20 μg/ml bis-benzamide, and 100 μg/ml yeast tRNA). Supernatants were collected from each sample and cells were disrupted by adding five ⅛" and one ⅜" stainless steel balls to each sample as well as 1 g 0.5 mm glass beads and shaking the samples for 4 minutes at 1500 strokes per minute in a Geno/Grinder 2000. Sodium chloride was added to each sample to 0.8 M, the sample was extracted once with phenol-chloroform, once with chloroform and precipitated in isopropanol.

Alternatively to filtration, formation water was first pelleted by centrifugation at 10,000 rpm for 30 minutes at 4° C., the supernatant removed into a fresh container, the cell/debris pellet suspended in lysis buffer and DNA purified in the same manner as described above. Residual biological material was recovered from the supernatant by adding polyethylene glycol 8000 to 10%, incubating at 4° C. overnight and then centrifuging at 10,000 rpm for 30 minutes at 4° C., suspending the pellet in lysis buffer and repeating the purification protocol described above. DNA obtained from the purifications was dissolved in a small volume of 10 mM Tris pH 8.0, 1 mM EDTA and analyzed by spectroscopy and gel electrophoresis.

Preparation of Genomic Library

A genomic library was constructed by shearing the metagenomic DNA from the pool of microorganisms above to 1-8 kb average size using a Genomic Solutions GeneMachines HydroShear equipped with a standard shearing assembly. The DNA was size-selected on agarose gels, joined to DNA adaptors and ligated into a medium-copy *E. coli* cloning vector using standard procedures known in the art. The ligation product was transformed into *E. coli* by electroporation, random clones were picked, grown in 1 ml cultures and plasmid DNA extracted. Each clone was sequenced bidirectionally using the Sanger method.

Sequence Analyses

The taxonomic diversity of the formation water (reservoir tank) was analyzed by comparing 16S gene sequences either directly from the metagenome (sequences from the environmental library) or by amplifying the 16S gene sequence from the DNA samples used for the metagenomic library construction. These analyses revealed a community composed of archaea and bacteria but no eukaryotic cells were present.

The individual metagenomic reads were then subjected to a proprietary bioinformatic annotation pipeline that first identified all open reading frames (ORFs) greater than 50 amino acids. To assign putative functions to each ORF, they were first analyzed for PFAM, TIGRFAM and SUPERFAM families against the current collections of multiple sequence alignments and Hidden Markov models for the respective protein families using the HMMER software. Additionally, BLASTp was used to compare proteins identified from the metagenome against the non-redundant protein database at GenBank. The annotation arising from this pipeline was then searched and a comparison between the metagenome reservoir tank, methane-producing enrichment cultures and isolated strains was performed. The analyses revealed a large number of genes that required oxygen such as dioxygenases (nitropropane, phytanoyl-CoA, toluate, Biphenyl 2,3-diol and diterpenoid), and monooxygenases (P450s, Alkane, ammonia and 2,4-dichloro). Along with oxygen requiring enzymes there were also substantial numbers of enzymes that help protect against oxygen such as catalases, superoxide dismutase, rubredoxin, and thioredoxin.

Figure 2A:
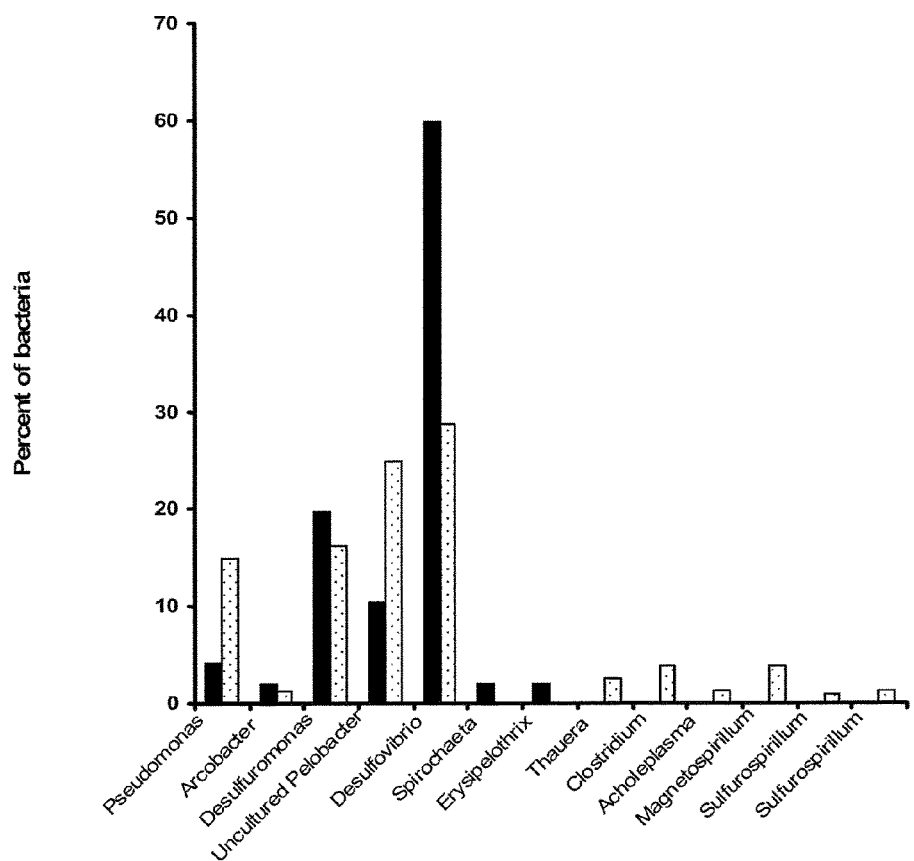
FIGS. 2A and 2B illustrate the bacterial and archaeal taxonomic composition of a representative methane-producing enrichment culture after 10 and 30 days in culture.
Figure 2B:
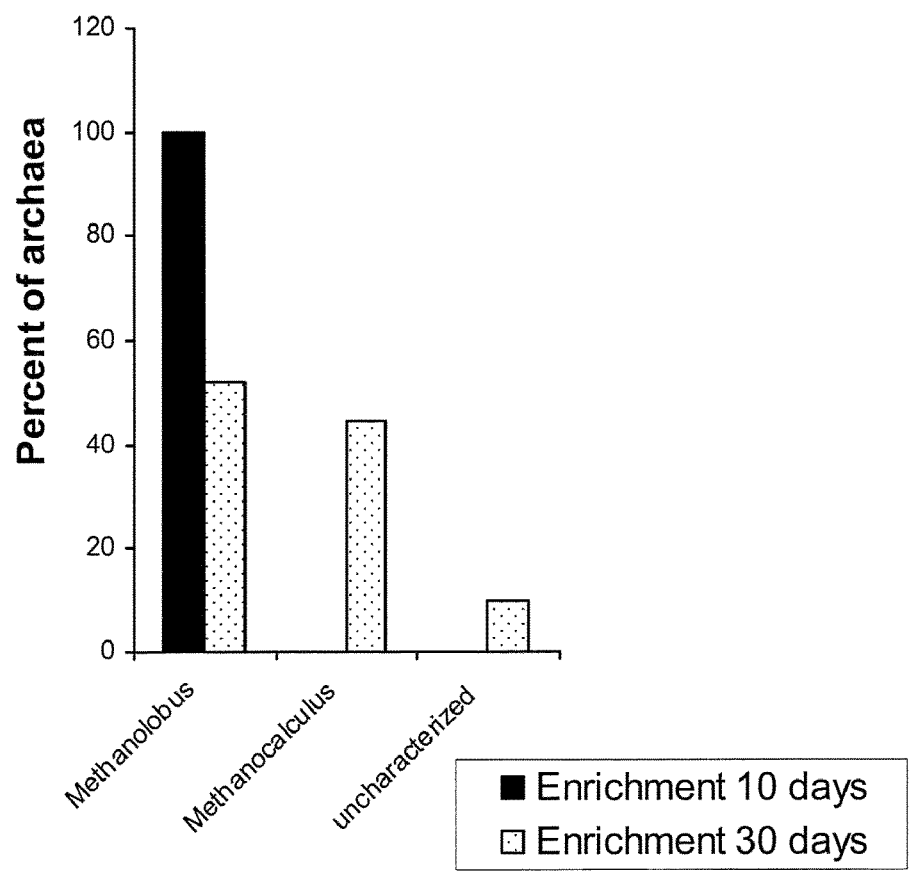
Figure 3:
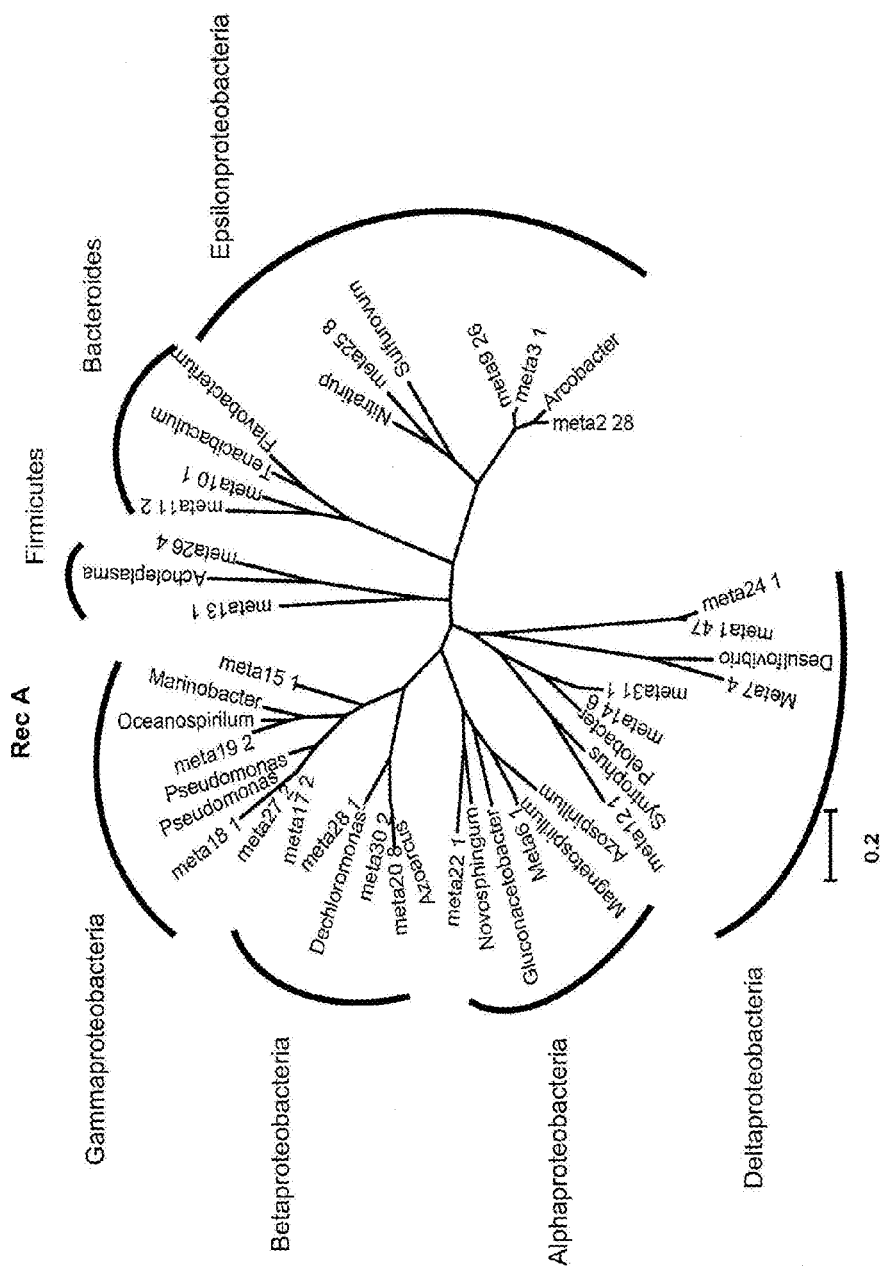
FIG. 3 illustrates the bacterial diversity in a representative sample of formation water as analyzed by the RecA gene sequences from the metagenome.

The methane-producing enrichment was analyzed taxonomically using 16S gene sequences for the Domains Bacteria and Archaea, the latter containing methanogens. The community was analyzed at 10 and 30 days of incubation by amplifying this fragment from the community, creating a library of 16S fragments by cloning them into a vector, transforming it into *E. coli* and sequenced the cloned fragments as described above. These sequences were then compared to public databases to see the closest cultivated relatives. As shown in FIG. 2A, the bacterial diversity was dominated by organisms related to *Pseudomonas, Desulfuromonas, Pelobacter, Desulfovibrio*, after 10 days and *Spirochaeta, Erysipelothrix, Thauera, Clostridium, Acholeplasma* and *Magnetospirillum* were less abundant at either 10 or 30 days. As shown in FIG. 2B, the archaeal population was dominated by the methanogen *Methanolobus* at day 10, and at day 30, *Methanocalculus* and a uncharacterized Crenarcheaota appeared. FIG. 3 illustrates the bacterial diversity in a representative sample of formation water as analyzed by the RecA gene sequences from the metagenome.

Well head samples—representation of bacterial 16S taxonomy

*Dictyoglomus*
*Planctomycetaceae*
*Rubrobacteraceae*
*Thermodesulfovibrio*
*Clostridiales*
*Bacteroidales*
*Thermacetogenium*
*Thermotoga*
*Thermosediminibacter*
*Deltaproteobacteria*
*Syntrophomonas*
*Bacteroidetes*
*Bacteroidales*
*Termodesulfovibrio*
*Magnetobacterium*
*Sporomusa*
*Deferribacteraceae*
*Thermotoga*
*Clostridiales*
*Sulfurospirillum*
*Proteiniphilum*
*Coprothermobacter*
*Anaerosinus*
*Azospira*
*Ceillonellaceae*
*Nitrospiracaea*
*Thermoanaerobacterium*
*Ruminococcaceae*
*Clostridia*
*Therminocola*
*Peptococcaceae*
*Clostridiales*
*Proteobacteria*
*Ralstonia*
*Ruminococcaceae*
*Bactersidales*
*Propionibacteriaceae*
*Niastella*
*Serratia*
*Thermodesulfovibrio*
*Niastella*
*Chryseobacterium*
*Smithella*
*Gammaproteobacteria*
*Magnetobacterium*
*Proteiniphilum*
*Spirochaetaceae*

Representation of archael 16S taxonomy—methanogenesis

*Thermoprotei*
*Methanothrix*
*Methanofollis*
*Methanobacterium*
*Methanomicrobiales*
*Methanocorpusculum*
*Desulfurococcales*

Strain Isolation

The functional enrichment and the environmental samples were used for the isolation of individual strains by environmental microbial compartmentalized cultivation (EMCC, as described in PCT/US2008/057919, WO2008/116187) or standard methods such as agar shakes. The EMCC method was done by encapsulating a cell suspension into gel microdroplets (GMDs) and incubating aerobically at 30° C. The cells formed colonies that were sorted into sterile media for subculturing. The resulting cell cultures were then analyzed by 16S to identify unique strains. The latter method consists of molten agar on which a cell suspension from a series of dilutions was applied. The tubes were then sealed and the headspace replaced with $N_2$:$CO_2$ or $H_2$:$O_2$ and incubated until cells start forming colonies which were picked and subcultured. Selected strains isolated were then cultured anaerobically, some of which have the ability to grow either aerobically or anaerobically.

To isolate the individual strains from the methane-producing enrichment, a sample of 100 µl was then diluted and inoculated into Hungate tubes with agar and coal to form colonies and provide for the isolation of specific lineages. Additionally, the enrichment was encapsulated and incubated aerobically for the formation of microcolonies which were arrayed into 96 well plates with a high speed cell sorter. These isolation efforts resulted in strains which were then identified using 16S gene sequences (as shown in FIGS. 2A and 2B). From this initial methane-producing enrichment, individual strains were culture for *Pseudomonas, Desulfuromonas, Pelobacter, Desulfovibrio, Thauera, Acholeplasma* and *Methanocalculus pumilus*. The individual strains could then be reconstituted into communities in a functional enrichment culture as defined microbial assemblages. Some isolated strains were also used for genome sequencing in order to identify genes and pathways involved in the degradation of coal. For example, a *Pseudomonas* strain exhibited oxygenases involved in the degradation of some PAHs such as 3-phenylpropanoate dioxygenase, alkanesulfonate monooxygenase, and catechol 2,3-dioxygenase among others.

Isolated cell cultures—16S taxonomy

| Assigned Genera (16S) | Cell cultures |
|---|---|
| *Acetobacterium* | 5 |
| *Acholeplasma* | 1 |
| *Achromobacter* | 5 |
| *Acinetobacter* | 1 |
| *Aeromonas* | 97 |
| *Aquimonas* | 1 |
| *Azoarcus* | 2 |
| *Azonexus* | 1 |
| *Azospira* | 82 |
| *Bacillus* | 47 |
| *Brevibacillus* | 15 |
| *Burkholderia* | 1 |
| *Butyrivibrio* | 2 |
| *Carnimonas* | 2 |
| *Citrobacter* | 9 |
| *Delftia* | 2 |
| *Desulfovibrio* | 2 |
| *Devosia* | 2 |
| *Dysgonomonas* | 3 |
| *Enterobacter* | 5 |
| *Ewingella* | 12 |
| *Geobacillus* | 43 |
| *Halomonas* | 3 |
| *Halovibrio* | 1 |
| *Hyphomonas* | 1 |
| *Levilinea* | 1 |

-continued

| Assigned Genera (16S) | Cell cultures |
|---|---|
| Methanocalculus | 1 |
| Micrococcineae | 1 |
| Nitrospira | 1 |
| Paenibacillus | 3 |
| Paludibacter | 1 |
| Pannonibacter | 2 |
| Parabacteroides | 3 |
| Petrotoga | 1 |
| Pseudomonas | 1636 |
| Raoultella | 3 |
| Rhodobacter | 2 |
| Rhodopseudomonas | 1 |
| Shewanella | 44 |
| Staphylococcus | 1 |
| Sulfurospirillum | 23 |
| Thalassospira | 7 |
| Thauera | 2 |
| Thiobacillus | 1 |
| Tistrella | 2 |
| unclassified_"Bacillaceae 2" | 1 |
| unclassified_Bacillus | 33 |
| unclassified_Bacteroidales | 2 |
| unclassified_Enterobacteriaceae | 1 |
| unclassified_Rhodocyclaceae | 1 |
| unclassified_Rikenellaceae | 3 |
| unclassified_Sphingomonadaceae | 1 |
| unclassified_Xanthomonadaceae | 1 |
| Vibrio | 2 |
| Wolinella | 2 |

Cultivation of Oxygen-Tolerant Microbial Strains from Formation Water

The inoculation of anaerobically-collected formation waters into aerobic media resulted in growth of various cell lines capable of assimilation of exogenous carbon sources such as yeast extract but notably, capable of growth on formation water and crude coal as sole carbon source. This suggested that there are cells in the environment with the genetic and physiological potential of aerobic hydrocarbon degradation. These strains included genetically diverse members of the group *Pseudomonas* such as *Pseudomonas* sp., *Pseudomonas* 3CB6, *Pseudomonas* sp. SCT, *Pseudomonas* sp. G-R2A7, and others such as *Hyphomonas polymorpha*, *Staphylococcus haemolyticus*, uncultured bacterium, uncultured denitrifying bacterium (*Thalassospira, Pannonibacter phragmatis* (Achromobacter), *Azoarcus* (Betaproteobacteria), *Tistrella mobilis*, and the uncultured bacterium (*Thaurea*). Many of these can grow in the presence of coal as sole carbon source and produce significant biomass.

Figure 4:
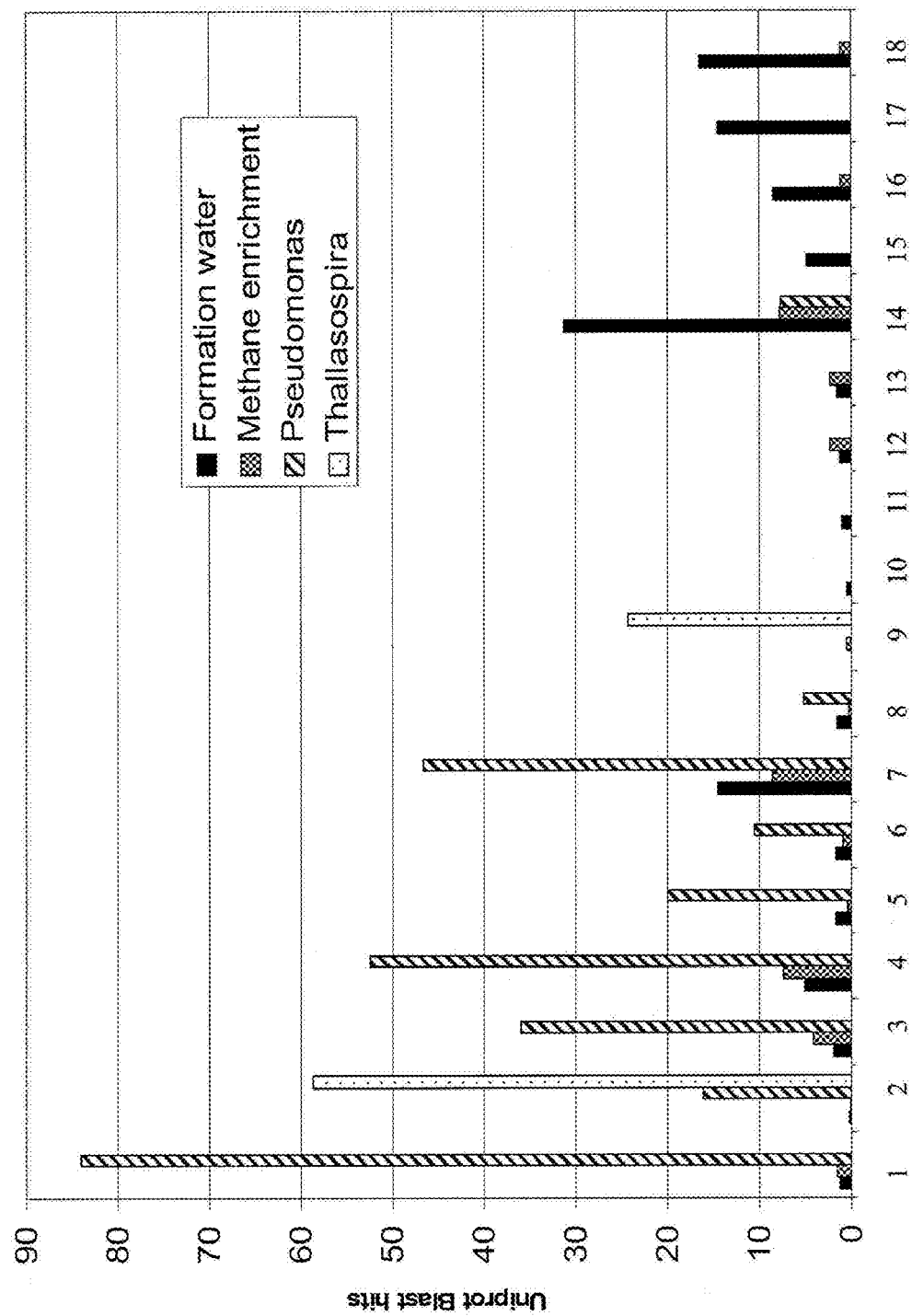
FIG. 4 illustrates and compares the profile of oxygenases in representative samples of formation water, a methane-producing enrichment culture, and two individual strains for which the genomes were sequenced. Sample numbers are as follows: 1=3-phenylpropanoate dioxygenase; 2=Phenylalanine 4-monooxygenase; 3=Biphenyl-2,3-diol 1,2-dioxygenase; 4=Alkanesulfonate monooxygenase; 5=Nitric oxide dioxygenase; 6=Biphenyl-2,3-diol 1,2-dioxygenase; 7=Catechol 2,3-dioxygenase; 8=Methane monooxygenase; 9=Homogentisate 1,2-dioxygenase; 10=Alkanal monooxygenase (FMN-linked); 11=Tryptophan 2,3-dioxygenase; 12=Benzene 1,2-dioxygenase; 13=Toluene dioxygenase; 14=Phenol 2-monooxygenase; 15=Tryptophan 2-monooxygenase; 16=2-chlorobenzoate 1,2-dioxygenase; 17=2,4-dichlorophenol 6-monooxygenase; and 18=Benzoate 1,2-dioxygenase.
Figure 5:
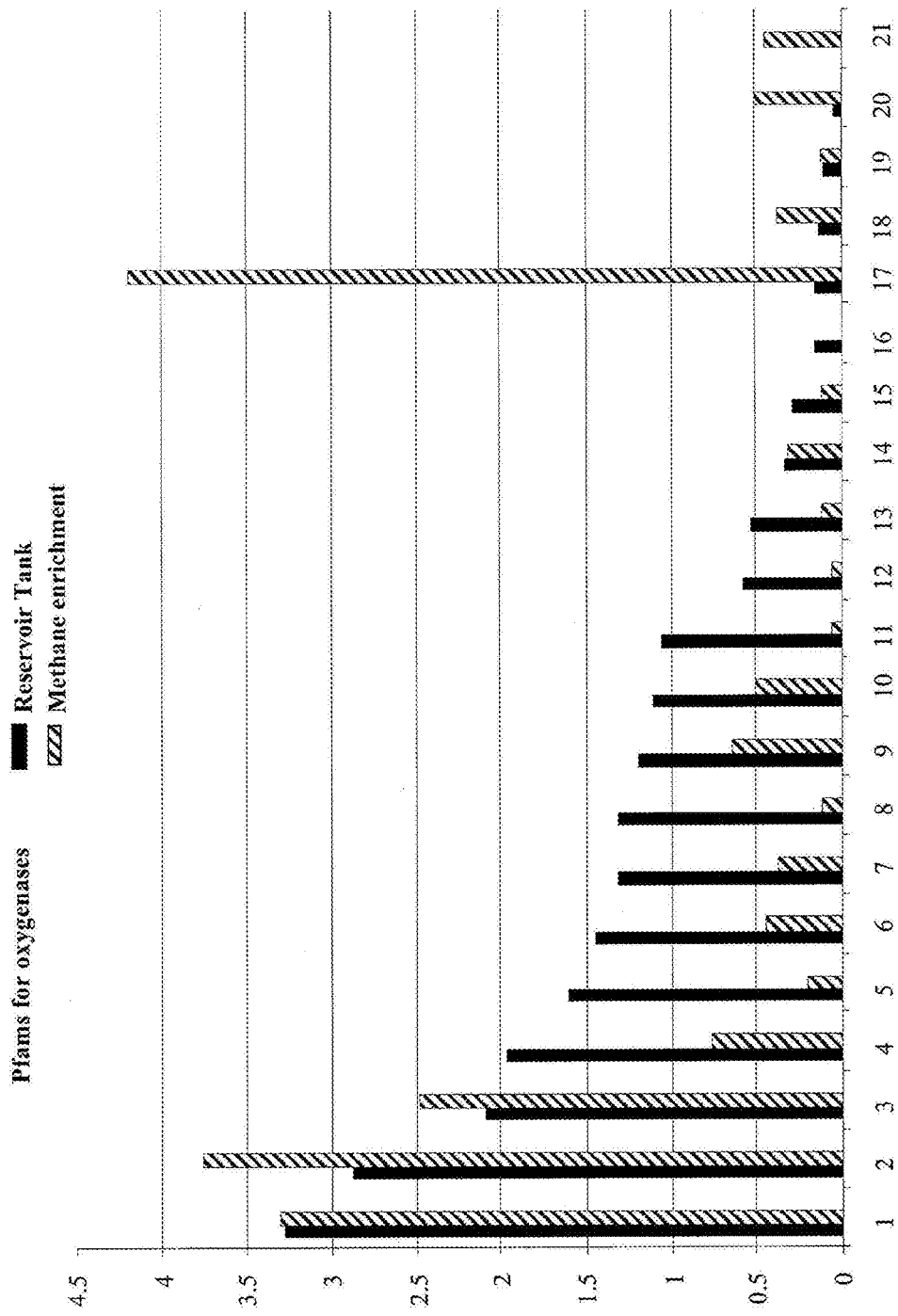
FIG. 5 illustrates and compares the profile of oxygenases in representative reservoir and methane-producing enrichment culture samples. Sample numbers are as follows: 1=Antibiotic biosynthesis monooxygenase; 2=LigB aromatic ring-opening dioxygenase 3=2OG-Fe(II) oxygenase superfamily; 4=Luciferase-like monooxygenase; 5=Ring hydroxylating dioxygenase alpha; 6=Putative ammonia monooxygenase; 7=Putative mono-oxygenase ydhR; 8=Phenol hydroxylase/oxygenase; 9=Phytanoyl-CoA dioxygenase (PhyH); 10=MmoB/DmpM monooxygenase family; 11=Phenol hydroxylase/monooxygenase; 12=Dioxygenase; 13=Phenylacetic acid dioxygenase; 14=ARD/ARD' acireductone dioxygenase; 15=Phenylacetic acid degradation oxygenase; 16=Aspartyl/Asparaginyl beta-hydroxylase/oxygenase; 17=Taurine catabolism dioxygenase TauD/TfdA; 18=homogentisate 1,2-dioxygenase; 19=Flavin-binding monooxygenase-like; 20=Heme oxygenase; and 21=Cysteine dioxygenase type I.
Figure 6:
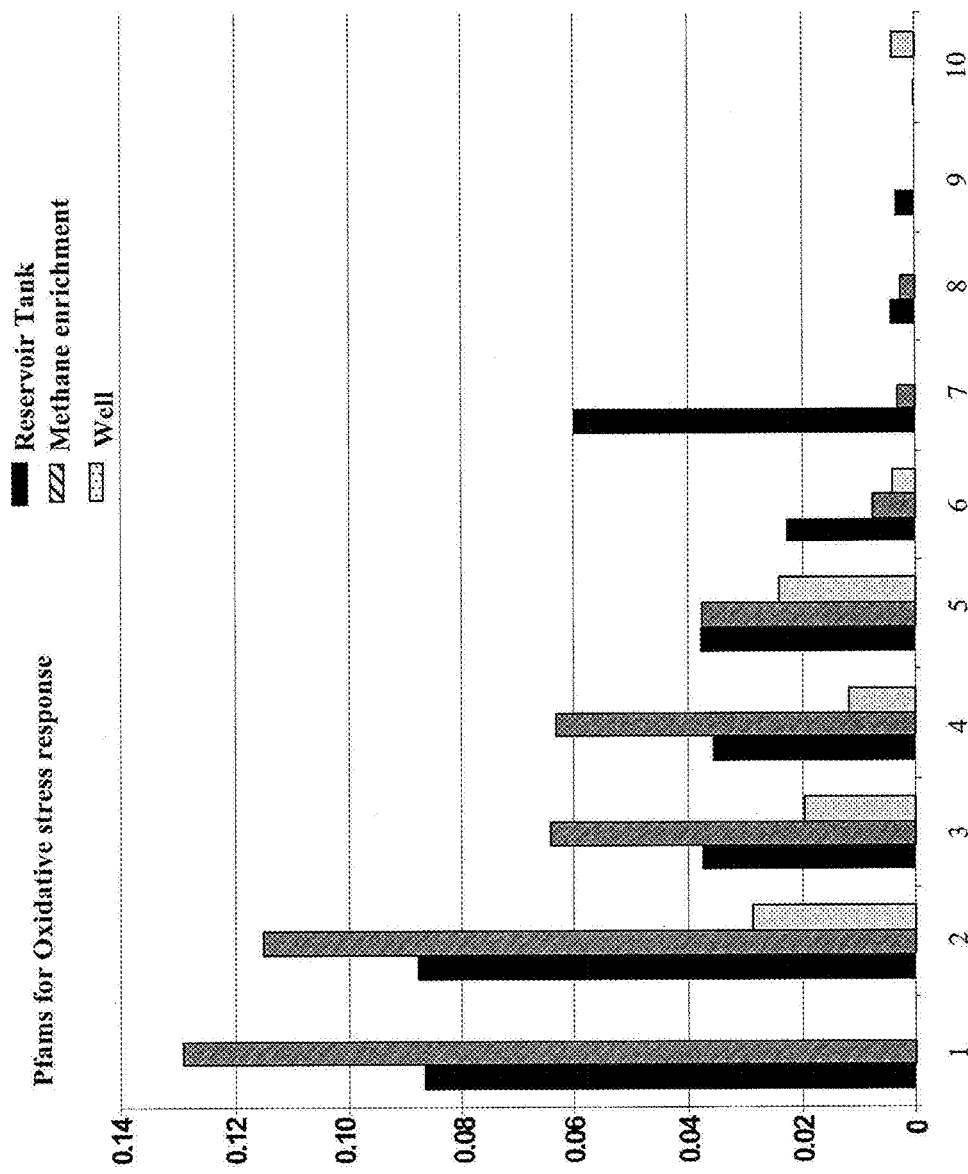
FIG. 6 illustrates and compares the profile of oxidative stress response enzymes in representative reservoir, methane-producing enrichment culture, and well samples. Sample numbers are as follows: 1=Di-haem cytochrome c peroxidase; 2=Peroxidase; 3=Iron/manganese superoxide dismutases, C-term; 4=Glutathione peroxidase; 5=Iron/manganese superoxide dismutases, alpha; 6=Catalase; 7=Paraquat-inducible protein A; 8=Copper/zinc superoxide dismutase (SODC); 9=Animal haem peroxidase; and 10=Manganese containing catalase.
Figure 7:
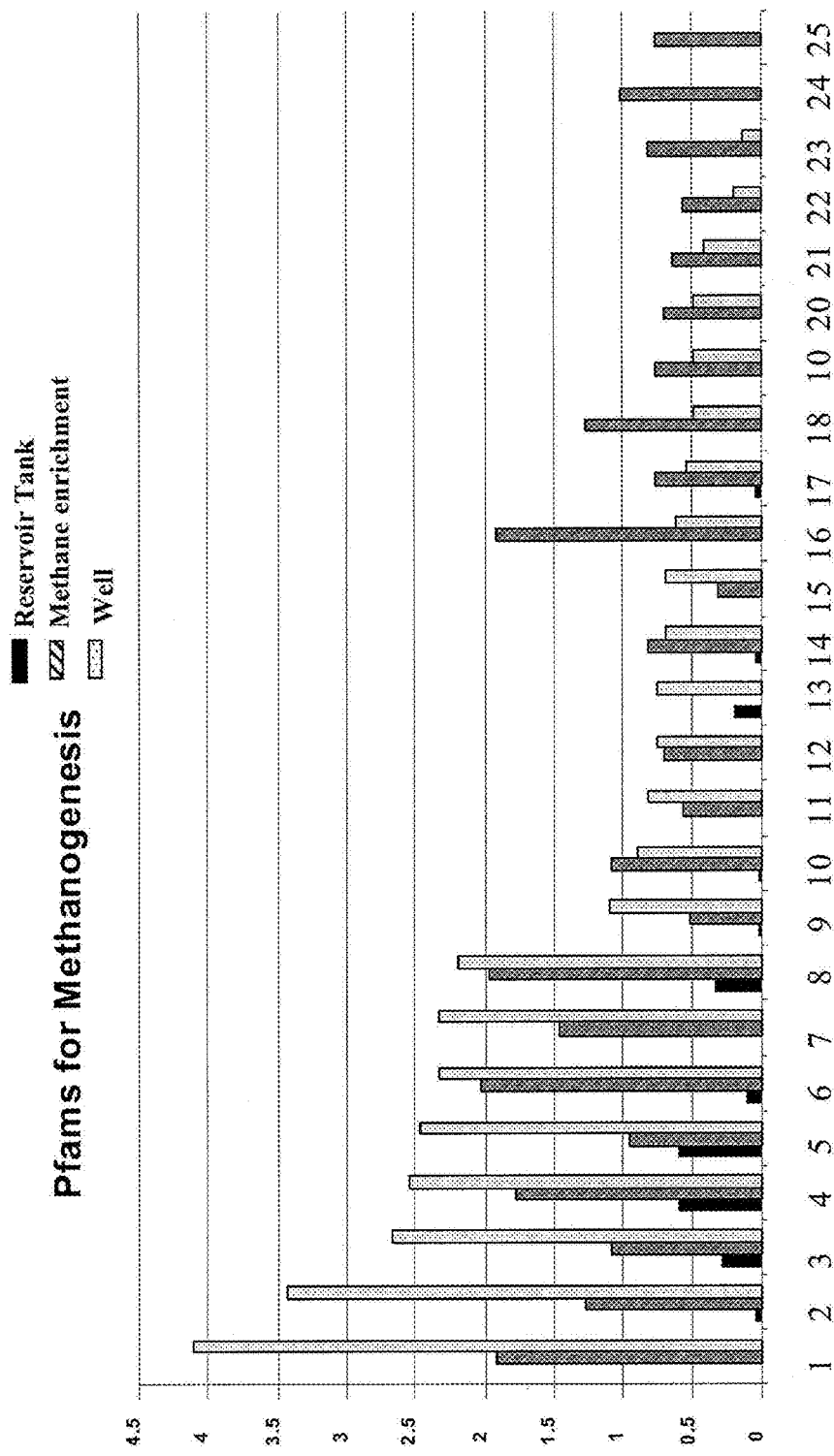
FIG. 7 illustrates and compares the profile of methanogenesis enzymes in representative reservoir, methane-producing enrichment culture, and well samples. Sample numbers are as follows: 1=Coenzyme F420 hydrogenase, beta C-term; 2=Coenzyme F420 hydrogenase, beta N-term; 3=Formyl-methanofuran-tetrahydromethanopterin formyltransferase; 4=Methenyl tetrahydromethanopterin cyclohydrolase; 5=Tungsten formylmethanofuran dehydrogenase, FwdE; 6=2-phosphosulpholactate phosphatase; 7=Tetrahydromethanopterin S-methyltransferase, H; 8=Formylmethanofuran—tetrahydromethanopterin formyltransferase; 9=Methyl-coenzyme M reductase gamma; 10=Methyl-coenzyme M reductase alpha C-term; 11=methylene tetrahydromethanopterin dehydrogenase; 12=Methyl-coenzyme M reductase beta C-term; 13=Methylene-tetrahydromethanopterin dehydrogenase, N-term; 14=Methyl-coenzyme M reductase alpha, N-term; 15=Methyl-coenzyme M reductase protein D; 16=Tetrahydromethanopterin S-methyltransferase, A; 17=Methyl-coenzyme M reductase protein C; 18=Domain of unknown function (DUF1894); 19=Tetrahydromethanopterin S-methyltransferase, E; 20=Tetrahydromethanopterin S-methyltransferase, B; 21=Methyl-coenzyme M reductase beta N-term; 22=Tetrahydromethanopterin S-methyltransferase, D; 23=Tetrahydromethanopterin S-methyltransferase, C; 24=Tetrahydromethanopterin S-methyltransferase, F; and 25=Tetrahydromethanopterin S-methyltransferase, G.
Figure 8:
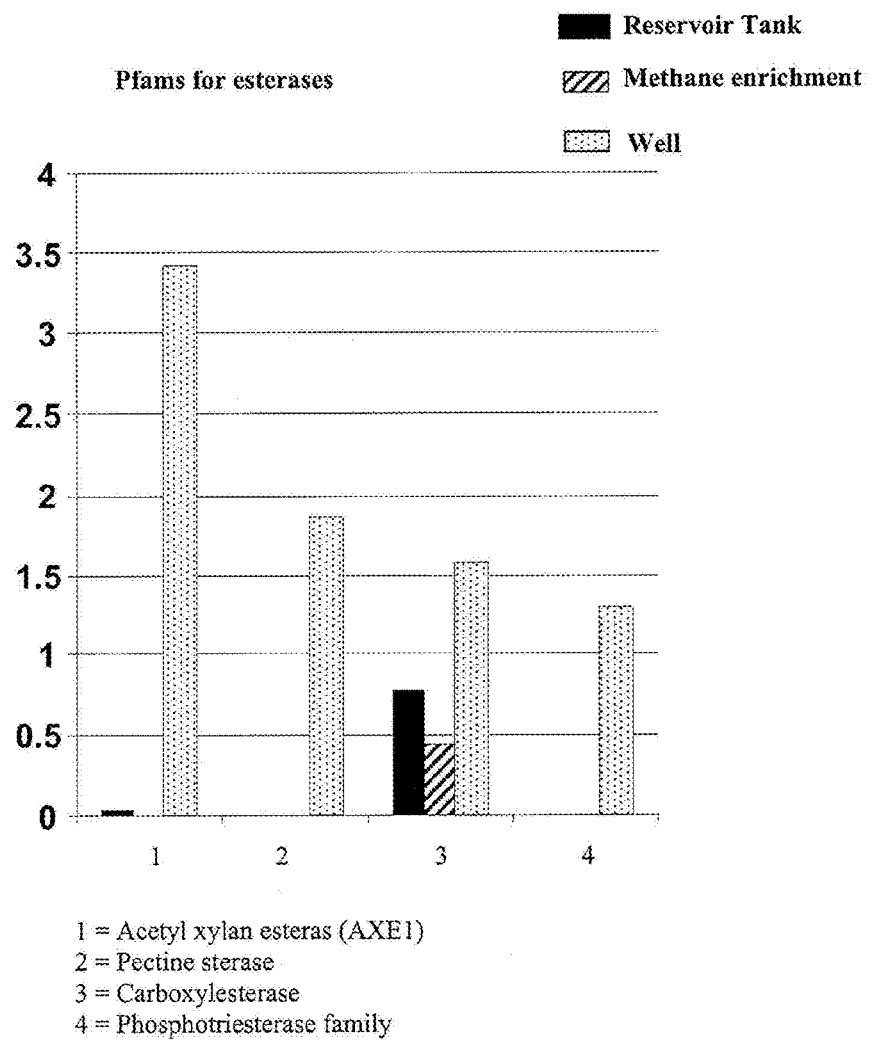
FIG. 8 illustrates and compares the profile of esterases in representative reservoir, methane-producing enrichment culture, and well samples.
Figure 9:
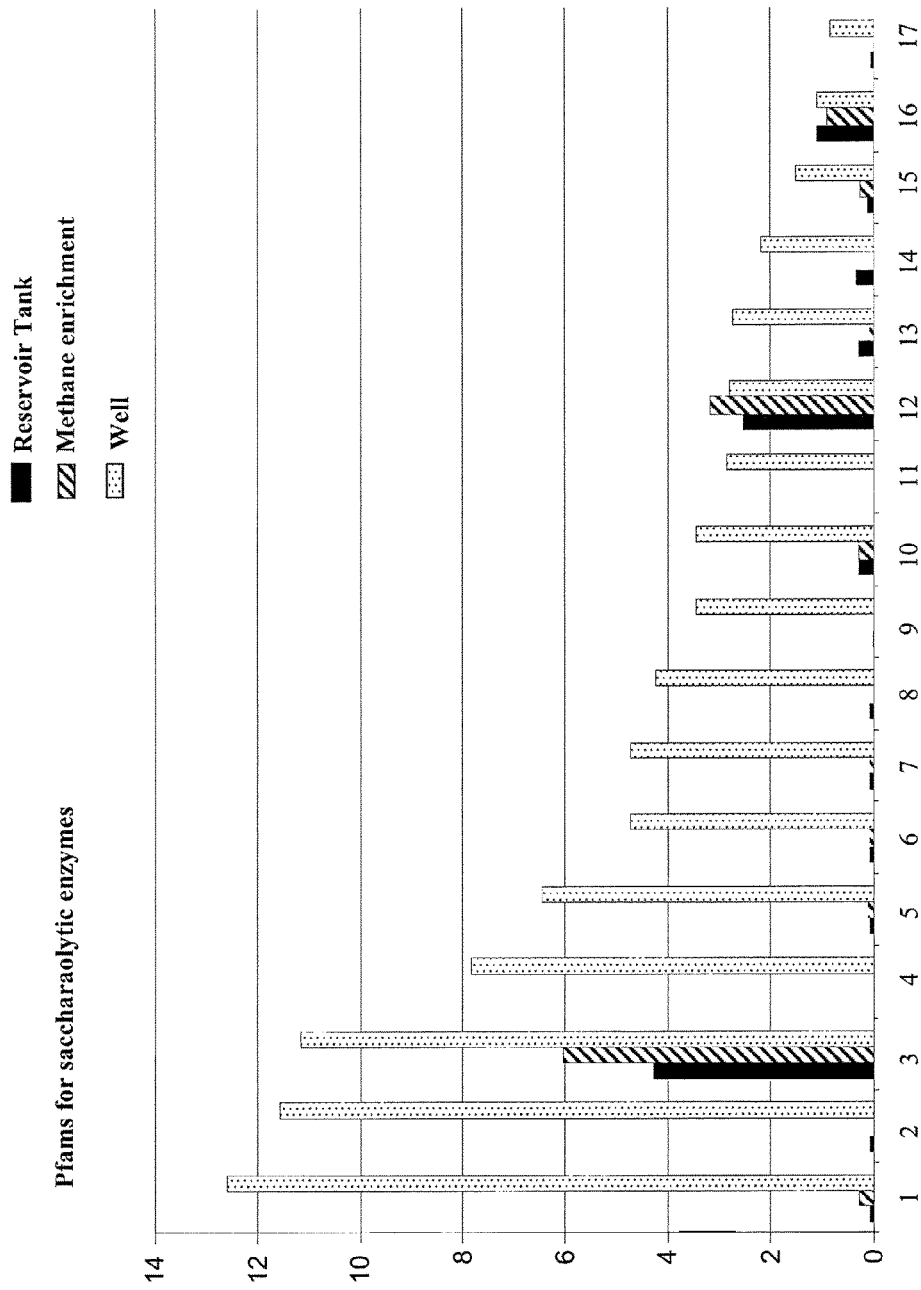
FIG. 9 illustrates and compares the profile of saccharaolytic enzymes in representative reservoir, methane-producing enrichment culture, and well samples. Sample numbers are as follows: 1=Cellulase (glycosyl hydrolase family 5); 2=-Putative glycosyl hydrolase (DUF1680); 3=Alpha amylase, catalytic domain; 4=Alpha-L-arabinofuranosidase C-terminus; 5=Alpha-L-fucosidase; 6=Bacterial alpha-L-rhamnosidase; 7=Bacterial alpha-L-rhamnosidase; 8=Beta galactosidase small chain; 9=Acetyl xylan esterase (AXE1); 10=PA14 domain; 11=Alpha-L-rhamnosidase N-terminal domain; 12=Isoamylase N-terminal domain; 13=Melibiase; 14=Alpha mannosidase, middle domain; 15=Amylo-alpha-1,6-glucosidase; 16=Alpha amylase, C-terminal all-beta domain; and 17=Bacterial pullanase-associated domain.
Figure 10:
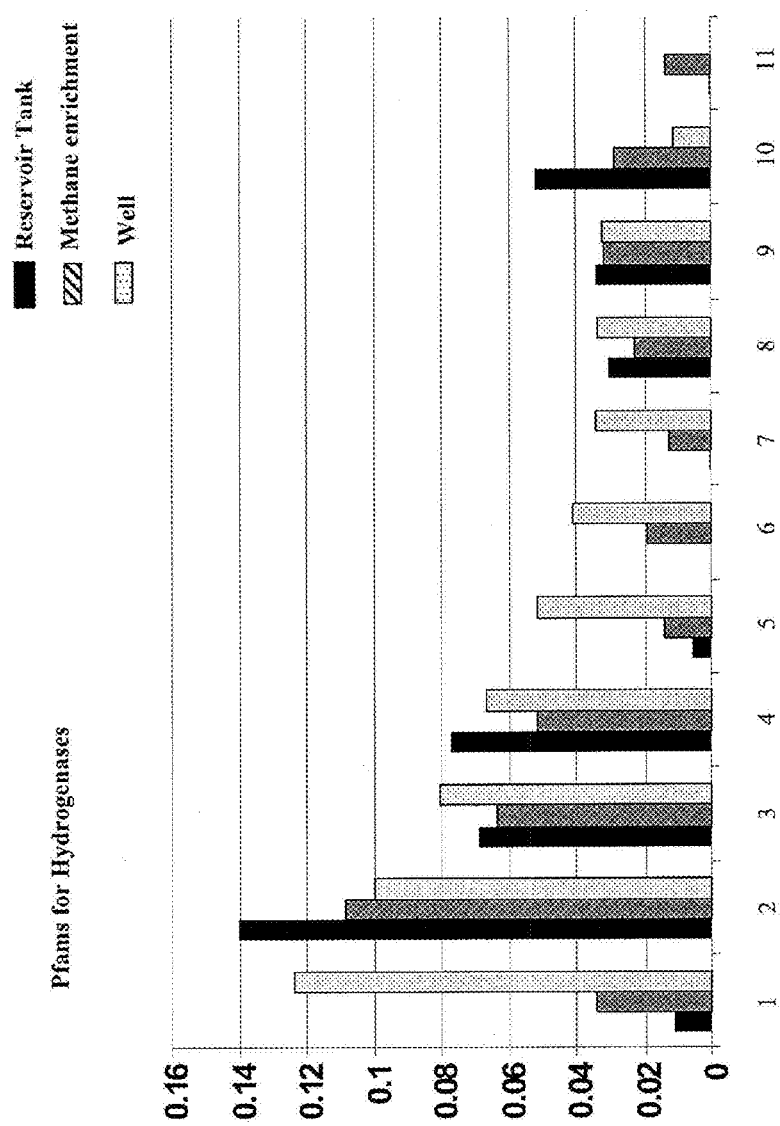
FIG. 10 illustrates and compares the profile of hydrogenases in representative reservoir, methane-producing enrichment culture, and well samples. Sample numbers are as follows: 1=Fe_hyd_lg_C; 2=NiFeSe_Hases; 3=HypD; 4=HYPF; 5=Fe_hyd_SSU; 6=FrhB_FdhB_C; 7=Frh-B_FdhB_N; 8=HypA; 9=HycL; 10=NiFe_dehyd_N; and 11=HyaE.
Figure 11:
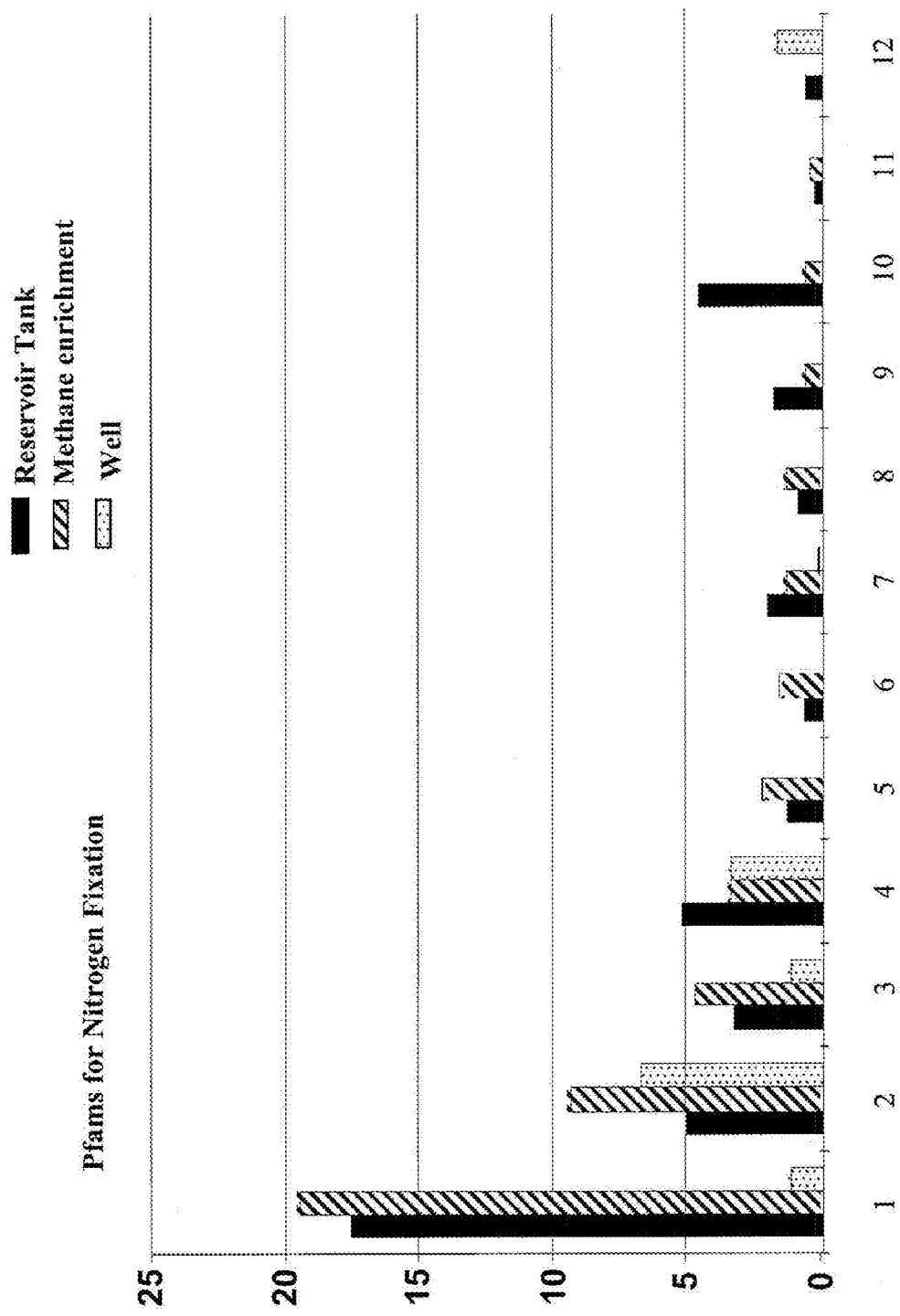
FIG. 11 illustrates and compares the profile of nitrogen fixation proteins in representative reservoir, methane-producing enrichment culture, and well samples. Sample numbers are as follows: 1=Nitrogenase Oxidoreductase; 2=Dinitrogenase iron-molybdenum cofactor; 3=Fer4 NifH; 4=NifU—unknown; 5=Dinitrogenase reductase ADP-ribosyltransferase (DRAT); 6=Nitrogen fixation protein NifW; 7=NifZ domain; 8=NifT/FixU protein; 9=Nitrogen fixation protein NifW; 10=Nif operon protein DUF269; 11=Nif operon protein (DUF683); and 12=NifQ.
Figure 12:
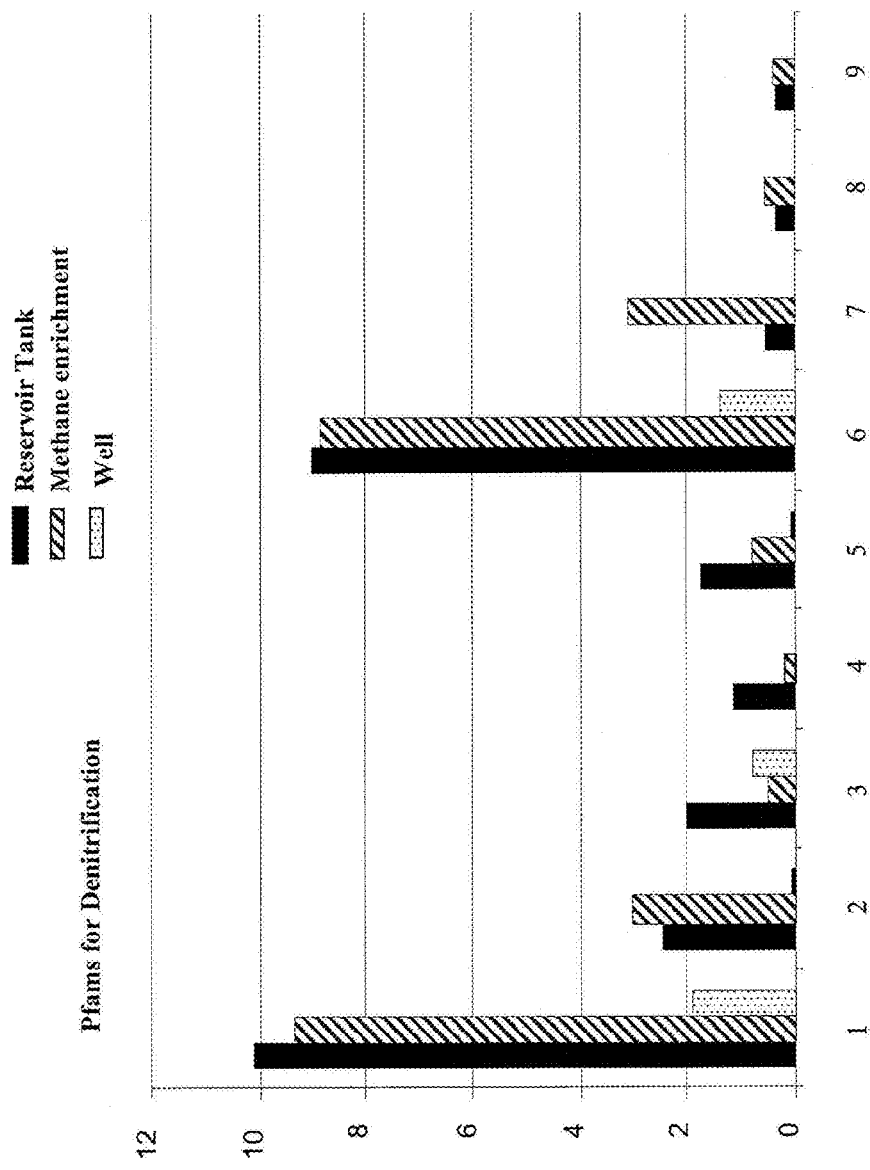
FIG. 12 illustrates and compares the profile of denitrification proteins in representative reservoir, methane-producing enrichment culture, and well samples. Sample numbers are as follows: 1=Nitrite and sulphite reductase 4Fe-4S domain; 2=Cytochrome D1 (nitrite reductase) heme domain; 3=Cytochrome c552 (nitrite reductase); 4=Nitrate reductase delta subunit; 5=Nitrate reductase gamma subunit; 6=Nitrite/Sulfite reductase ferredoxin-like half domain; 7=Nitrate reductase cytochrome c-type subunit (NapB); 8=NapD protein; and 9=Periplasmic nitrate reductase protein NapE.

The coalbed methane sites and their associated formation waters are thought to be anoxic and current paradigms indicate the dominant metabolism appears to be related to fermentations and the anaerobic respiration of nitrate, sulfate and other terminal electron acceptors but not oxygen. However the metagenomic analyses of the formation water revealed microorganisms may be amenable to cultivation using formation water as mineral base and coal as sole carbon source and various combinations of electron acceptors including oxygen nitrate, sulfate, or iron-phosphate to stimulate microbial respiration. As shown in FIG. 4, broad representations of monooxygenases and dioxygenases were found in samples of formation water, methane enrichment cultures, as well as isolated strains of *Pseudomonas* and *Thallasospira*.

Identification of Enzyme Families

Metagenomic data obtained from samples of reservoir and methane enrichment cultures allowed the identification of several classes of enzymes that could serve as interventions to increase the production of methane from hydrocarbon-bearing formations. Table 1 below provides the Pfams of enzyme families that have been identified which function at various enzymatic steps in the conversion of hydrocarbon to coal. FIGS. 5-12 further illustrate the diversity of enzymes identified in a number of Pfams.

TABLE 1

| Metabolic process | Organism | Enzyme |
|---|---|---|
| Low-rank-coal hydrolysis | Dictyoglomus Thermotoga Desulfurococcales | PF02446 4-alpha-glucanotransferase
PF05448 Acetyl xylan esterase (AXE1)
PF02806 Alpha amylase, C-terminal all-beta domain
PF02903 Alpha amylase, N-terminal ig-like domain
PF09261 Alpha mannosidase, middle domain
PF07821 Alpha-amylase C-terminal beta-sheet domain
PF09071 Alpha-amylase, C terminal
PF05270 Alpha-L-arabinofuranosidase B (ABFB)
PF09206 Alpha-L-arabinofuranosidase B, catalytic
PF06964 Alpha-L-arabinofuranosidase C-terminus
PF08531 Alpha-L-rhamnosidase N-terminal domain
PF06202 Amylo-alpha-1,6-glucosidase
PF05592 Bacterial alpha-L-rhamnosidase
PF05592 Bacterial alpha-L-rhamnosidase
PF03714 Bacterial pullanase-associated domain
PF02929 Beta galactosidase small chain
PF02449 Beta-galactosidase
PF08533 Beta-galactosidase C-terminal domain
PF08532 Beta-galactosidase trimerisation domain
PF03856 Beta-glucosidase (SUN family)
PF02018 Carbohydrate binding domain
PF02839 Carbohydrate binding domain
PF03425 Carbohydrate binding domain (family 11)
PF03426 Carbohydrate binding domain (family 15)
PF03424 Carbohydrate binding domain (family 17/28)
PF03427 Carbohydrate binding domain (family 19)
PF03423 Carbohydrate binding domain (family 25)
PF09478 Carbohydrate binding domain CBM49
PF03422 Carbohydrate binding module (family 6)
PF09212 Carbohydrate binding module 27
PF00553 Cellulose binding domain
PF00942 Cellulose binding domain
PF02013 Cellulose or protein binding domain
PF01607 Chitin binding Peritrophin-A domain
PF00182 Chitinase class I
PF03174 Chitobiase/beta-hexo- |

TABLE 1-continued

| Metabolic process | Organism | Enzyme |
|---|---|---|
| | | saminidase C-terminal domain |
| | | PF06452 Domain of unknown function(DUF1083) |
| | | PF09081 Domain of unknown function(DUF1921) |
| | | PF09154 Domain of unknown function(DUF1939) |
| | | PF09260 Domain of unknown function(DUF1966) |
| | | PF02056 Family 4 glycosyl hydrolase |
| | | PF00734 Fungal cellulose binding domain |
| | | PF09137 Glucodextranase, domain N |
| | | PF07915 Glucosidase II beta subunit-like protein |
| | | PF03198 Glycolipid anchored surface protein |
| | | PF00232 Glycosyl hydrolase family1 |
| | | PF00331 Glycosyl hydrolase family10 |
| | | PF01670 Glycosyl hydrolase family12 |
| | | PF01373 Glycosyl hydrolase family14 |
| | | PF00728 Glycosyl hydrolase family20, catalytic domain |
| | | PF02838 Glycosyl hydrolase family20, domain 2 |
| | | PF02156 Glycosyl hydrolase family26 |
| | | PF01915 Glycosyl hydrolase family 3 C terminal domain |
| | | PF00933 Glycosyl hydrolase family 3 N terminal domain |
| | | PF02015 Glycosyl hydrolase family45 |
| | | PF01374 Glycosyl hydrolase family46 |
| | | PF01532 Glycosyl hydrolase family47 |
| | | PF02011 Glycosyl hydrolase family48 |
| | | PF03718 Glycosyl hydrolase family49 |
| | | PF03512 Glycosyl hydrolase family52 |
| | | PF07745Glycosyl hydrolase family 53 |
| | | PF03065Glycosyl hydrolase family 57 |
| | | PF02057 Glycosyl hydrolase family59 |
| | | PF03443 Glycosyl hydrolase family61 |
| | | PF03664Glycosyl hydrolase family 62 |
| | | PF03632 Glycosyl hydrolase family65 central catalytic domain |
| | | PF03633 Glycosyl hydrolase family 65, C-terminal domain |
| | | PF03636 Glycosyl hydrolase family 65, N-terminal domain |
| | | PF07477 Glycosyl hydrolase family 67 C-terminus |
| | | PF07488 Glycosyl hydrolase family 67 middle domain |
| | | PF03648 Glycosyl hydrolase family 67 N-terminus |
| | | PF00840 Glycosyl hydrolase family 7 |
| | | PF02324 Glycosyl hydrolase family70 |
| | | PF03659 Glycosyl hydrolase family71 |
| | | PF03663 Glycosyl hydrolase family76 |
| | | PF03662 Glycosyl hydrolase family 79, N-terminal domain |
| | | PF03639 Glycosyl hydrolase family81 |
| | | PF03644 Glycosyl hydrolase family85 |
| | | PF07470 Glycosyl Hydrolase Family88 |
| | | PF00759 Glycosyl hydrolase family 9 |
| | | PF07971 Glycosyl hydrolase family92 |
| | | PF08306 Glycosyl hydrolase family98 |
| | | PF08307 Glycosyl hydrolase family 98 C-terminal domain |
| | | PF00457 Glycosyl hydrolases family11 |
| | | PF00723 Glycosyl hydrolases family15 |
| | | PF00722 Glycosyl hydrolases family 16 |
| | | PF00332 Glycosyl hydrolases family 17 |
| | | PF00704 Glycosyl hydrolases family 18 |
| | | PF00703 Glycosyl hydrolases family 2, immunoglobulin-like beta-sandwich domain |
| | | PF02837 Glycosyl hydrolases family 2, sugar binding domain |
| | | PF02836 Glycosyl hydrolases family 2, TIM barrel domain |
| | | PF01183 Glycosyl hydrolases family 25 |
| | | PF00295 Glycosyl hydrolases family 28 |
| | | PF01055 Glycosyl hydrolases family 31 |
| | | PF08244 Glycosyl hydrolases family 32 Cterminal |
| | | PF00251 Glycosyl hydrolases family 32 Nterminal |
| | | PF01301 Glycosyl hydrolases family 35 |
| | | PF07748 Glycosyl hydrolases family 38 C-terminal domain |
| | | PF01074 Glycosyl hydrolases family 38 N-terminal domain |
| | | PF01229 Glycosyl hydrolases family 39 |
| | | PF04616 Glycosyl hydrolases family 43 |
| | | PF01341 Glycosyl hydrolases family 6 |
| | | PF01270 Glycosyl hydrolases family 8 |
| | | PF01630 Hyaluronidase |
| | | PF02922 Isoamylase N-terminal domain |
| | | PF02435 Levansucrase/Invertase |
| | | PF03200 Mannosyl oligosaccharide glucosidase |
| | | PF02065 Melibiase |
| | | PF08305 NPCBM/NEW2 domain |
| | | PF02927 N-terminal ig-like domain of cellulase |
| | | PF02055 O-Glycosyl hydrolase family 30 |
| | | PF07691 PA14 domain |
| | | PF09113 Peptide-N-glycosidase F, C terminal |
| | | PF09112 Peptide-N-glycosidase F, N terminal |
| | | PF01522 Polysaccharide |

TABLE 1-continued

| Metabolic process | Organism | Enzyme |
|---|---|---|
| | | deacetylase |
| | | PF03173 Putative carbohydrate binding domain |
| | | PF03173 Putative carbohydrate binding domain |
| | | PF06204 Putative carbohydrate binding domain |
| | | PF07944 Putative glycosyl hydrolase of unknown function (DUF1680) |
| | | PF03370 Putative phosphatase regulatory subunit |
| | | PF00686 Starch binding domain |
| Coal Depolymerization | Chlostridium Petrotoga Planctomycetaceae | PF05448-Acetyl xylan esterase (AXE1) |
| | | PF01095-Pectinesterase |
| | | PF00135-Carboxylesterase |
| | | Chelatases |
| | | Production of low-molecular-weight organic acids |
| Anaerobic (or aerobic) degradation of PAHs | Thermoprotei Anaerovorax Smithella Anaerobaculum Thermacetogenium Aeromonas Dechloromonas Pseudomonas Thauera Marinobacter Alcanivorax Desulfuromonas Desulfovibrio Spirochaeta Azoarcus | PF00067 Cytochrome P450 |
| | | PF00171 Aldehyde dehydrogenase family |
| | | PF00775 Dioxygenase |
| | | PF00848 Ring hydroxylating alpha subunit (catalytic domain) |
| | | PF00866 Ring hydroxylating beta subunit |
| | | PF01188 Mandelate racemase/muconate lactonizing enzyme, C-terminal domain |
| | | PF01231 Indoleamine 2,3-dioxygenase |
| | | PF01361 Tautomerase enzyme |
| | | PF01596 O-methyltransferase |
| | | PF01689 Hydratase/decarboxylase |
| | | PF01731 Arylesterase |
| | | PF01738 Dienelactone hydrolase family |
| | | PF01869 BadF/BadG/BcrA/BcrD ATPase family |
| | | PF01883 Domain of unknown function DUF59 |
| | | PF02332 Methane/Phenol/Toluene Hydroxylase |
| | | PF02426 Muconolactone delta-isomerase |
| | | PF02461 Ammonia monooxygenase |
| | | PF02578 Uncharacterised ACR, YfiH family COG1496 |
| | | PF02626 Allophanate hydrolase subunit 2 |
| | | PF02627 Carboxymuconolactone decarboxylase family |
| | | PF02668 Taurine catabolism dioxygenase TauD, TfdA family |
| | | PF02746 Mandelate racemase/muconate lactonizing enzyme, N-terminal domain |
| | | PF02798 Glutathione S-transferase, N-terminal domain |
| | | PF02900 Catalytic LigB subunit of aromatic ring-opening dioxygenase |
| | | PF02962 5-carboxymethyl-2-hydroxymuconate isomerase |
| | | PF03079 ARD/ARD' family |
| | | PF03171 2OG-Fe(II) oxygenase superfamily |
| | | PF03241 4-hydroxyphenylacetate 3-hydroxylase family |
| | | PF03301 Tryptophan 2,3-dioxygenase |
| | | PF03349 Outer membrane protein transport protein (OMPP1/FadL/TodX) |
| | | PF03594 Benzoate membrane transport protein |
| | | PF04209 homogentisate 1,2-dioxygenase |
| | | PF04303 Protein of unknown function (DUF453) |
| | | PF04444 Catechol dioxygenase N terminus |
| | | PF04663 Phenol hydroxylase conserved region |
| | | PF04744 Monooxygenase subunit B protein |
| | | PF04896 Ammonia monooxygenase/methane monooxygenase, subunit C |
| | | PF05145 Putative ammonia monooxygenase |
| | | PF05494 Toluene tolerance, Ttg2 |
| | | PF05721 Phytanoyl-CoA dioxygenase (PhyH) |
| | | PF05870 Phenolic acid decarboxylase (PAD) |
| | | PF06052 3-hydroxyanthranilic acid dioxygenase |
| | | PF06099 Phenol hydroxylase subunit |
| | | PF06234 Toluene-4-monooxygenase system protein B (TmoB) |
| | | PF06917 Periplasmic pectate lyase |
| | | PF07424 TrbM |
| | | PF07746 Aromatic-ring-opening dioxygenase LigAB, LigA subunit |
| | | PF07976 Phenol hydroxylase, C-terminal dimerisation domain |
| | | PF08201 BssC/TutF protein |
| | | PF08282 haloacid dehalogenase-like hydrolase |
| | | PF08803 Putative monooxygenase ydhR |
| | | PF08883 Dopa 4,5-dioxygenase family |
| | | PF09448 Methylmuconolactone methyl-isomerase |
| | | PF09459 Ethylbenzene dehydrogenase |
| | | PF09662 Phenylphosphate carboxylase gamma subunit (Phenyl_P_gamma) |
| Homo-acetogenesis | | PF01268 formyltetrahydrofolate synthetase |
| | | PF03598 CO dehydrogenase/acetyl-CoA synthase complex beta subunit |
| | | PF03599 CO dehydrogenase/acetyl-CoA synthase delta subunit |
| Methanogenesis (hydrogenotrophic and acetoclastic) | Methanothrix Methanosarcina Methanofolis Methanobacterium Methanolobus Methanocalculus Methanomicrobiales Methanocorposculum Methanosarcina | PF01913 Formylmethanofuran-tetrahydromethanopterin formyltransferase |
| | | PF01993 methylene tetrahydromethanopterin dehydrogenase |
| | | PF02007 Tetrahydromethanopterin S-methyltransferase, H |
| | | PF02240 Methyl-coenzyme M reductase gamma |
| | | PF02241 Methyl-coenzyme M reductase beta C-term |
| | | PF02249 Methyl-coenzyme M reductase alpha C-term |
| | | PF02289 Methenyl tetrahydromethanopterin cyclohydrolase |
| | | PF02505 Methyl-coenzyme M reductase protein D |
| | | PF02663 Tungsten formylmethanofuran dehydrogenase, FwdE |
| | | PF02741 Formylmethanofuran-- |

TABLE 1-continued

| Metabolic process | Organism | Enzyme |
|---|---|---|
| | | tetrahydromethanopterin formyltransferase |
| | | PF02745 Methyl-coenzyme M reductase alpha, N-term |
| | | PF02783 Methyl-coenzyme M reductase beta N-term |
| | | PF04029 2-phosphosulpholactate phosphatase |
| | | PF04206 Tetrahydromethanopterin S-methyltransferase, E |
| | | PF04207 Tetrahydromethanopterin S-methyltransferase, D |
| | | PF04208 Tetrahydromethanopterin S-methyltransferase, A |
| | | PF04210 Tetrahydromethanopterin S-methyltransferase, G |
| | | PF04211 Tetrahydromethanopterin S-methyltransferase, C |
| | | PF04422 Coenzyme F420 hydrogenase beta N-term |
| | | PF04432 Coenzyme F420 hydrogenase, beta C-term |
| | | PF04609 Methyl-coenzyme M reductase protein C |
| | | PF05440 Tetrahydromethanopterin S-methyltransferase, B |
| | | PF08979 Domain of unknown function (DUF1894) |
| | | PF09176 Methylene-tetrahydromethanopterin dehydrogenase, N-term |
| | | PF09472 Tetrahydromethanopterin S-methyltransferase, F |

Example 3

Stimulation of Methane Production

Figure 13:
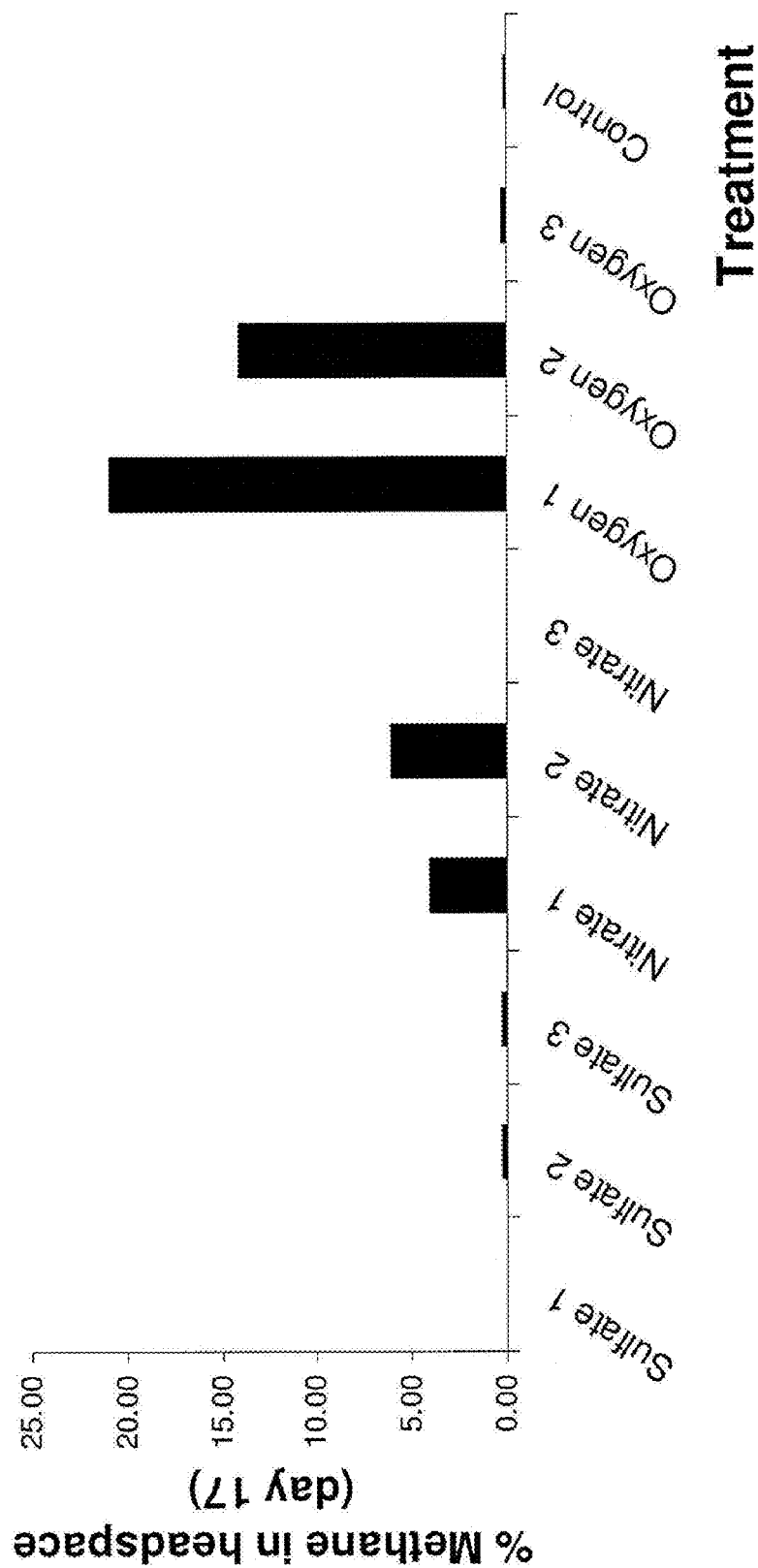
FIG. 13 illustrates increased methane production by a defined microbial assemblage after stimulation with various electron acceptors and oxygen.

The availability of a defined microbial assemblage producing methane from coal in vitro, as well as a suite of strains capable of aerobic coal degradation prompted laboratory experiments where various stimulants were tested for their effect on methane production. FIG. 13 shows the results of stimulation of the culture system with varying amounts of oxygen (2%, 4%, and 10% $O_2$), and electron acceptors sulfate (at 0.1 mM, 1 mM and 10 mM) and nitrate (at 0.1 mM, 1 mM and 10 mM).

The greatest increase in methane production was observed in response to limited pulses of oxygen suggesting a limiting factor for methane production from coal may be the electron flow derived from aerobic hydrocarbon degradation. This degradation is stimulated by the addition of oxygen as reactant for the oxygenase-classes of enzymes present in some of the strains included in the DMA. However, when oxygen is applied at higher than optimal levels it represses methanogenesis possibly due to replacing $CO_2$ as terminal electron acceptor and/or oxidation of oxygen-sensitive enzymes either in methanogens or other anaerobic microbial groups.

Table 2 below provides a list of the putative oxygenases and corresponding host organisms identified by the 16S genomic analyses.

TABLE 2

| Putative oxygenase | Putative host organisms |
|---|---|
| 2,3-dihydroxyphenylpropionate 1,2-dioxygenase | *Bradyrhizobium* sp. ORS278 |

TABLE 2-continued

| Putative oxygenase | Putative host organisms |
|---|---|
| 2-nitropropane dioxygenase, NPD | *Alkaliphilus metalliredigens* QYMF] |
| 2OG-Fe(II) oxygenase | *Methylobacillus flagellatus* KT] |
| 4-hydroxyphenylpyruvate dioxygenase | *Pseudomonas aeuruginosa* PA7] |
| Alkane 1-monooxygenase | *Pseudomonas mendocina* ymp} |
| Antibiotic biosynthesis monooxygenase | *Candidatus Desulfococcus oleovorans* Hxd3] |
| benzoate 1,2 diosygenase, alpha subunit | *Burkholderia pseudomallei* 668] |
| aromatic ring-opening dioxygenase | *Pseudomonas entomophila* L48] |
| Biphenyl-2,3-diol 1,2 dioxygenase III-related protein | *Vibrio cholerae* O1 biovar eltor str. N1696] |
| Catalytic LigB subunit of aromatic ring-opening dioxygenase | *Leptospira borgpetersenii* se rovar Hardjo-bovis L55] |
| Catechol 2,3-dioxygenase | *Azoarcus* sp. BH72] |
| Cyclohexanone monooxygenase | *Parvibaculum lavamentivorans* DS-1] |
| dioxygenases related to 2-nitropropane diosygenase | *Pseudomonas entomophila* L48] |
| diterpenoid dioxygenase | *Mycobacterium* sp. JLS] |
| Extradiol ring-cleavage dioxygenase, class III enzyme, subunit | *Caldicellulosiruptor saccharolyticus* DSM 8903] |
| Glyoxalase/bleomycin resistance protein/dioxygenase | *Dechloromonas aromatica* RCB] |
| homogentisate 1,2-dioxygenase | *Chromobacterium violaceum* ATCC 12472] |
| luciferase-like monooxygenase | *Burkholderia mallei* NCTC 10247] |
| Phenylacetate-CoA oxygenase, PaaG subunit | *Burkholderia pseudomallei* 1710b] |
| probable ring-hydroxylating dioxygenase subunit | *Pseudomonsa aeruginosa* PAO1] |
| Putative ammonia monooxygenase | *Jannaschia* sp. CCS1] |
| Putatvie Extradiol ring-cleavage dioxygenase | *Bradyrhizobium* sp. BTAi1] |
| Putative protocatechuate 3,4-dioxygenase beta chain protein | *Vibrio parahae molyticus* RIMD 2210633 |
| toluate 1,2-dioxsygenase electron transfer component | *Pseudomonas aeruginosa* PA7] |

FIG. 4 compares the profile of monooxygenases and dioxygenases detected by 16S genomic analyses of the formation water microorganisms, the methane enrichment culture, as well as isolated strains of *Pseudomonas* and *Thallasospira*.

The addition of oxygen to the DMA can only result in an increase in methane formation if the strict anaerobic members are not affected. Oxygen tolerance of anaerobic bacteria and niethanogenic archaea have been described recently (Boga, H. I. and Brune, A. 2003. Hydrogen-dependent oxygen reduction by homoacetogenic bacteria isolated from termite guts. Appl. Environ. Microbiol. 69:779-786) and the tolerance towards oxygen of pure culture composing the DMA can be tested.

Figure 14:
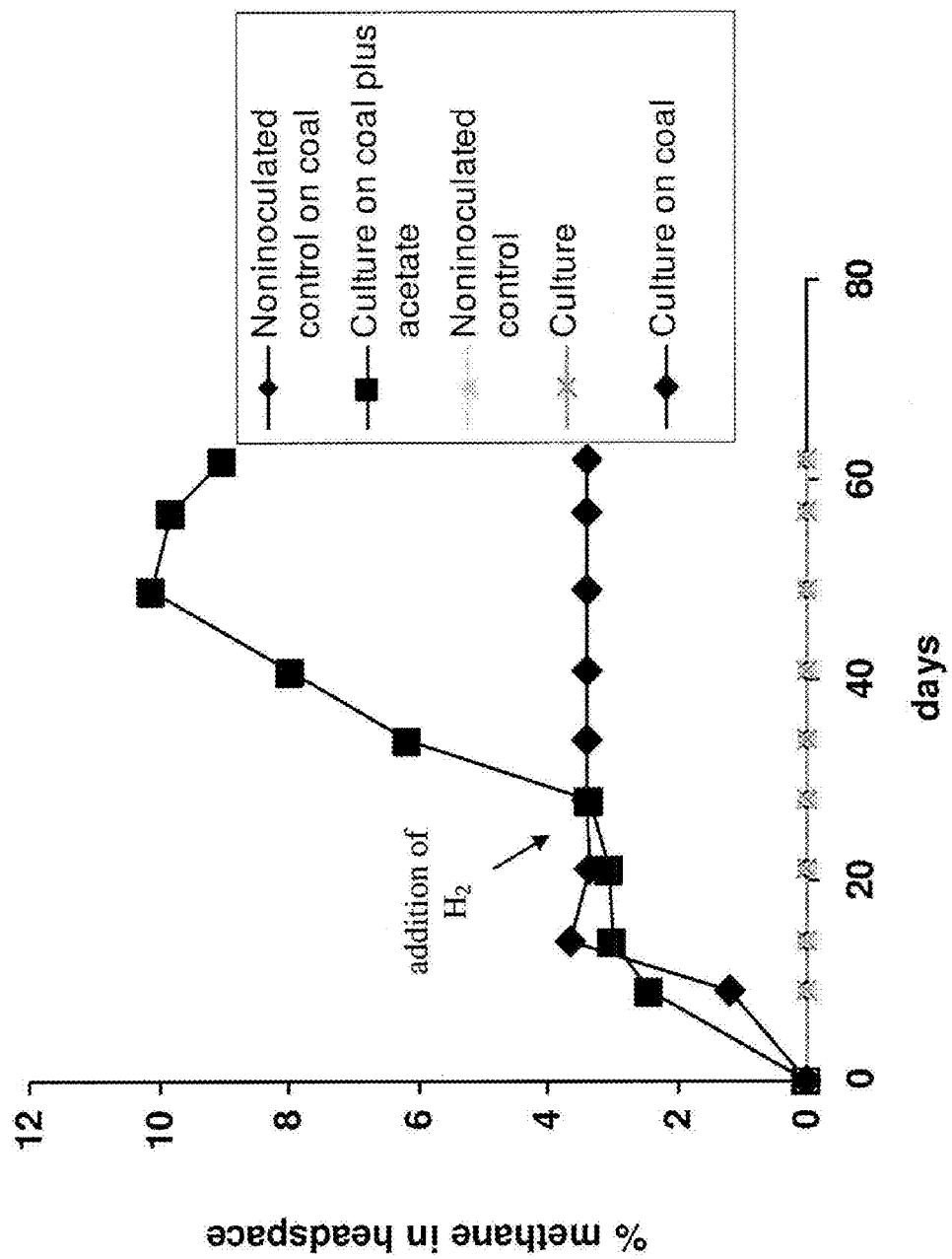
FIG. 14 illustrates increased methane production by a defined microbial assemblage after stimulation with hydrogen and acetate.

FIG. 14 shows increased methane production following stimulation with $H_2$ and acetate in cultures grown using coal as the sole carbon source.

Figure 15:
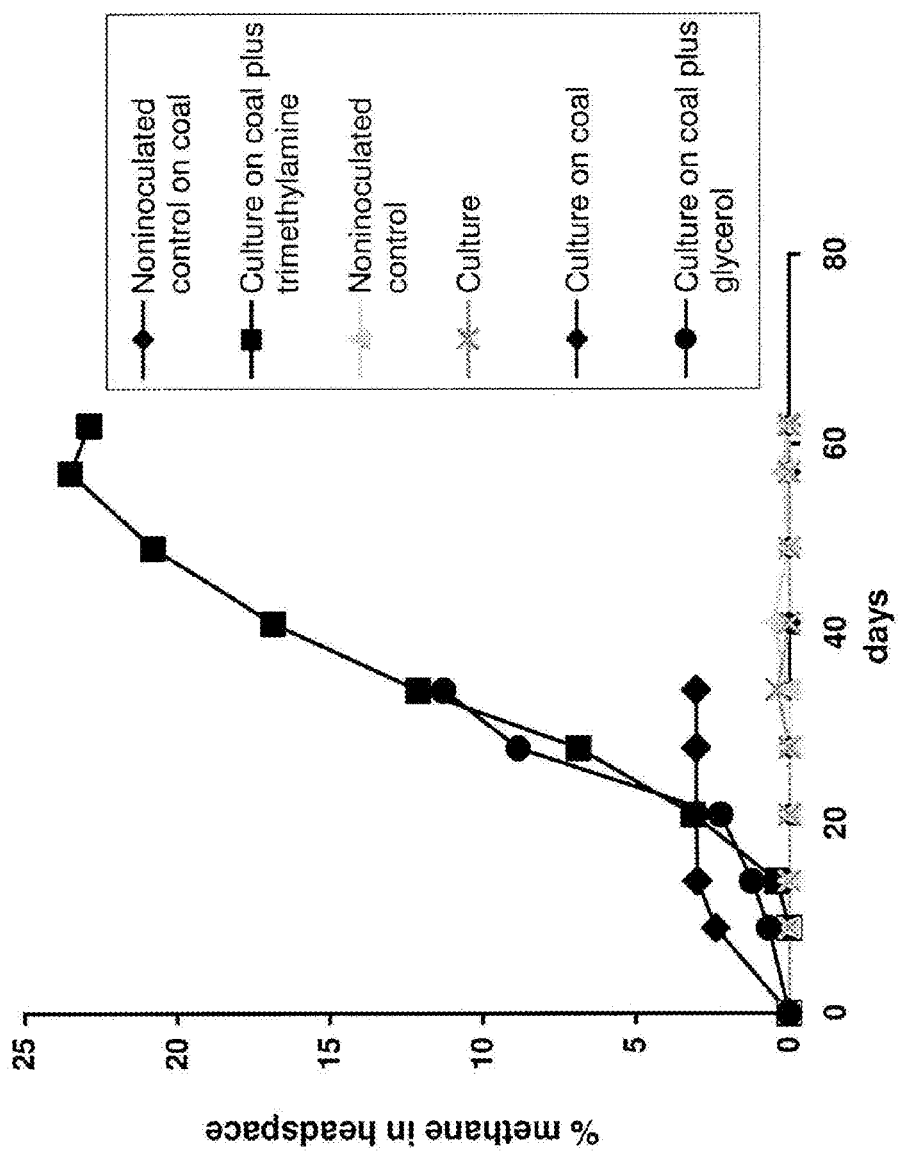
FIG. 15 illustrates increased methane production by a defined microbial assemblage after stimulation with glycerol or trimethylamine.

FIG. 15 shows increased methane production following stimulation with trimethylamine in cultures grown using coal as the sole carbon source.

All publications and patent applications mentioned in this specification are herein incorporated by reference to the same extent as if each individual publication or patent application was specifically and individually indicated to be incorporated by reference.

What is claimed is:

1. A method of identifying a stimulant that increases biogenic production of methane in a hydrocarbon-bearing formation comprising:
    (a) obtaining a nucleic acid sequence from one or more microorganisms derived from a hydrocarbon-bearing formation environment;

(b) determining the presence of one or more gene products of a nucleic acid sequence from one or more microorganisms derived from a hydrocarbon-bearing formation environment, wherein said gene product is an enzyme in a pathway involved in the conversion of a hydrocarbon to methane selected from the group consisting of peroxidases, phenol oxidases, alcohol oxidases, laccases, hydrolases, glycosyl hydrolases, esterases, etherases, oxidases, nitrogenases, cellulases, amylases, glucanaeses, pullanases, reductases, dismutases, oxygenases, monooxygenases, dioxygenases, calatases, hydrogenases, carboxylases, and methyl reductases; or an enzyme involved in homoacetogenesis, methanogenesis, aceto-clastic methanogenesis or $CO_2$-reducing methanogenesis; and (c) identifying a substrate, reactant or co-factor of said enzyme that acts as a stimulant to increase methane production when provided to one or more microorganisms in said hydrocarbon-bearing formation as compared with methane production in the absence of the stimulant.

2. A method according to claim 1, wherein said one or more microorganisms are enriched by selecting for the ability to grow on coal as the sole carbon source.

3. A method according to claim 1, wherein step (c) comprises testing in vitro one or more substrate, reactant or cofactor at more than one concentration to monitor and optimize methane production in a culture system comprising at least one microorganism isolated from said hydrocarbon-bearing formation, further wherein said culture system provides coal as the sole carbon source.

4. A method according to claim 3, wherein said at least one microorganism is a bacterial species or an archaeal species capable of converting a hydrocarbon to a product selected from the group consisting of hydrogen, carbon dioxide, acetate, formate, methanol, methylamine, and a methanogenic substrate; a methanogenic bacterial species; or a methanogenic archaeal species.

5. A method according to claim 3, wherein said at least one microorganism is a species of bacteria selected from the genus group consisting of *Pseudomonas, Arcobacter, Desulfuromonas, Pelobacter, Desulfovibrio, Spirochaeta, Erysipelothrix, Thauera, Clostridium, Acholeplasma, Magnetospirillum,* and *Sulfurospirillum*; or a species of archaea selected from the group consisting of *Methanolobus, Methanocalculus,* and members of the phylum *Crenarcheaota.*

6. A method according to claim 1, wherein step (c) comprises testing in vitro one or more substrate, reactant or cofactor at more than one concentration to monitor and optimize methane production in a culture system comprising a defined microbial assemblage; wherein said defined microbial assemblage combines a culture of a single strain of microorganism from a hydrocarbon-bearing formation with at least one other defined culture of another single strain of microorganism, such that members of said defined microbial assemblage act synergistically to produce methane; and further wherein said culture system provides coal as the sole carbon source.

7. A method according to claim 6, wherein said defined microbial assemblage comprises at least two species of microorganisms selected from the genus group consisting of *Pseudomonas, Arcobacter, Desulfuromonas, Pelobacter, Desulfovibrio, Spirochaeta, Erysipelothrix, Thauera, Clostridium, Acholeplasma, Magnetospirillum, Sulfurospirillum; Methanolobus, Methanocalculus,* and members of the phylum *Crenarcheaota.*

8. A method according to claim 1, wherein said hydrocarbon-bearing formation is selected from the group consisting of coal, peat, lignite, oil shale, oil formation, traditional black oil, viscous oil, oils sands and tar sands.

9. A method according to claim 1, wherein said enzyme is selected from the group consisting of oxygenases, monooxygenases, and dioxygenases.

10. A method according to claim 1, wherein said substrate, reactant or co-factor is selected from the group consisting of a sulfur-containing compound, a nitrogen-containing compound, a phosphorous-containing compound, a trace element, an electron acceptor, an electron donor, a halogen, a metal, an alcohol, an organic acid, an alkane, an alkene, an alkyne, an aromatic compound, an amine, an ether, an aldehyde, a ketone, a thiol, acetate, an aromatic hydrocarbon, and a gas.

11. A method according to claim 9, wherein said substrate, reactant or co-factor is oxygen.

\* \* \* \* \*